US011844717B2

(12) United States Patent
O'Grady et al.

(10) Patent No.: US 11,844,717 B2
(45) Date of Patent: Dec. 19, 2023

(54) NUTRIENT RECYCLING DEVICE

(71) Applicant: THE INSIDES COMPANY LIMITED, Auckland (NZ)

(72) Inventors: Gregory Brian O'Grady, Auckland (NZ); John Bilkey Davidson, Auckland (NZ); Robert Bruce Davidson, Auckland (NZ); Ian Peter Bissett, Auckland (NZ); Mackenzie Liam Greenslade, Auckland (NZ)

(73) Assignee: THE INSIDES COMPANY LIMITED, Auckland (NZ)

( * ) Notice: Subject to any disclaimer, the term of this patent is extended or adjusted under 35 U.S.C. 154(b) by 355 days.

(21) Appl. No.: 16/754,476

(22) PCT Filed: Oct. 9, 2018

(86) PCT No.: PCT/IB2018/057792
§ 371 (c)(1),
(2) Date: Apr. 8, 2020

(87) PCT Pub. No.: WO2019/073365
PCT Pub. Date: Apr. 18, 2019

(65) Prior Publication Data
US 2020/0390590 A1    Dec. 17, 2020

(30) Foreign Application Priority Data

Oct. 9, 2017 (NZ) ........................................ 736237
Nov. 15, 2017 (NZ) ........................................ 737381

(51) Int. Cl.
*A61F 5/44* (2006.01)
*A61J 15/00* (2006.01)
*A61F 5/443* (2006.01)

(52) U.S. Cl.
CPC ............ *A61F 5/4405* (2013.01); *A61F 5/443* (2013.01); *A61F 5/4407* (2013.01); *A61J 15/0076* (2015.05); *A61J 15/0092* (2013.01)

(58) Field of Classification Search
CPC . A61J 15/003; A61J 15/00; A61M 2025/0233
(Continued)

(56) References Cited

U.S. PATENT DOCUMENTS 1,217,567 A    2/1917 Clare
2,524,750 A    10/1950 Bellinger
(Continued)

FOREIGN PATENT DOCUMENTS

CN    204233499 U    4/2015
CN    106310407 A    1/2017
(Continued)

OTHER PUBLICATIONS

K. Al-Harbi et al., "Mucous Fistula Refeeding in Neonates With Short Bowel Syndrome," Journal of Pediatric Surgery, vol. 34, No. 7 (July), 1999, pp. 1100-1103.
(Continued)

*Primary Examiner* — Susan S Su
*Assistant Examiner* — Ted Yang
(74) *Attorney, Agent, or Firm* — McCarter & English, LLP

(57) ABSTRACT

A nutrient recycling device is provided that is configured to collect digestive contents from a first opening of a gastro-intestinal (GI) tract and recycle and/or return the digestive contents to a second location in a patient's gastrointestinal tract. The device and associated method may find application in patients with a number of complaints, such as short bowel syndrome and/or prior to stoma reversal surgery. The device comprises a bag adapted to receive the digestive contents from a first GI opening, and a pump incorporated
(Continued)

with the bag adapted to pump the digestive contents to a second GI location. The pump includes an inlet in fluid communication with the interior of the bag, and an outlet connected to an outlet conduit adapted to provide a flow pathway for the digestive content to flow from the pump to second GI location.

30 Claims, 12 Drawing Sheets

(58) Field of Classification Search
USPC .................................................. 604/35, 910
See application file for complete search history.

(56) References Cited

U.S. PATENT DOCUMENTS

| | | | |
|---|---|---|---|
| 3,042,041 A | 7/1962 | Jascalevich | |
| 3,298,610 A | 1/1967 | Hirano | |
| 3,937,224 A | 2/1976 | Uecker | |
| 4,356,824 A * | 11/1982 | Vazquez | A61J 15/0069 604/35 |
| 4,983,102 A | 1/1991 | Swain | |
| 6,093,869 A | 7/2000 | Roe et al. | |
| 6,447,472 B1 * | 9/2002 | Moss | A61M 1/734 604/27 |
| 6,840,923 B1 | 1/2005 | Lapcevic | |
| 7,294,120 B1 | 11/2007 | Eidsen et al. | |
| 7,648,479 B2 * | 1/2010 | Solovay | A61M 39/26 604/128 |
| 7,666,171 B2 | 2/2010 | Mombrinie et al. | |
| 8,808,221 B2 | 8/2014 | Kamen et al. | |
| 10,028,893 B2 | 7/2018 | Kane et al. | |
| 10,136,979 B2 | 11/2018 | Forsell | |
| 10,166,139 B2 | 1/2019 | Logier et al. | |
| 10,568,998 B2 | 2/2020 | Akkerman et al. | |
| 2004/0006320 A1 * | 1/2004 | Buglino | A61F 5/448 604/344 |
| 2006/0264829 A1 * | 11/2006 | Donaldson | A61M 5/142 604/890.1 |
| 2006/0270970 A1 * | 11/2006 | Moss | A61J 15/0076 604/35 |
| 2008/0195047 A1 | 8/2008 | Price | |
| 2012/0130341 A1 | 5/2012 | Whitley | |
| 2015/0351954 A1 * | 12/2015 | Logier | A61F 5/445 604/335 |
| 2018/0353318 A1 | 12/2018 | Logier et al. | |

FOREIGN PATENT DOCUMENTS

| | | |
|---|---|---|
| CN | 106798962 A | 6/2017 |
| CN | 107080612 A | 8/2017 |
| GB | 2539890 A | 1/2017 |

OTHER PUBLICATIONS

E. Levy et al., "High-Ouput external fistulae of the small bowel: management with continuous enteral nutrition," Br. J. Surg., 1989, vol. 76, July, pp. 676-679.

K. Schafer et al., "Continuous extracorporeal stool-transport system: a new and economical procedure for transito short-bowel syndrome in prematures and newborns," Pediatr. Surg. Int., (1997) 12, pp. 73-75.

* cited by examiner

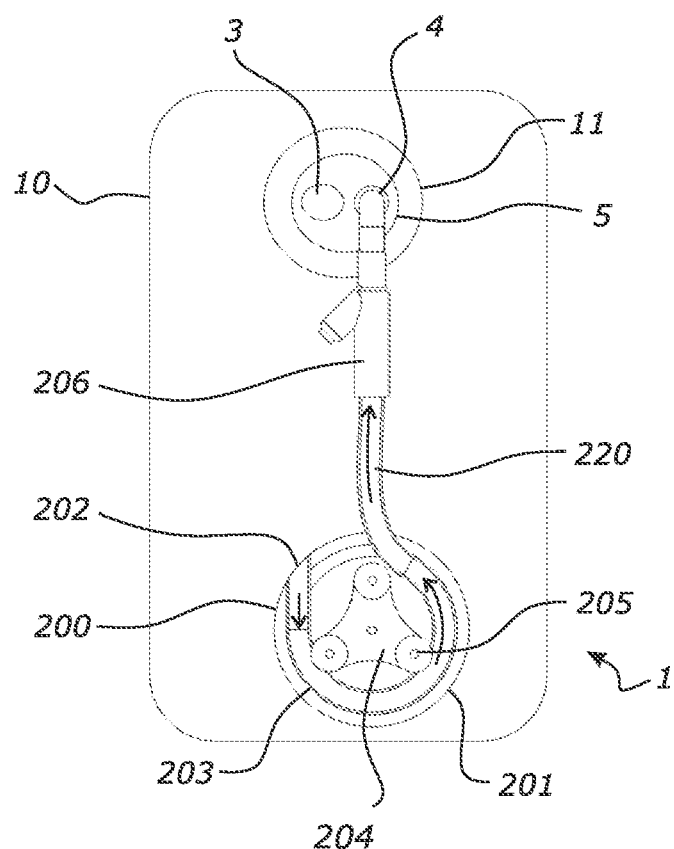
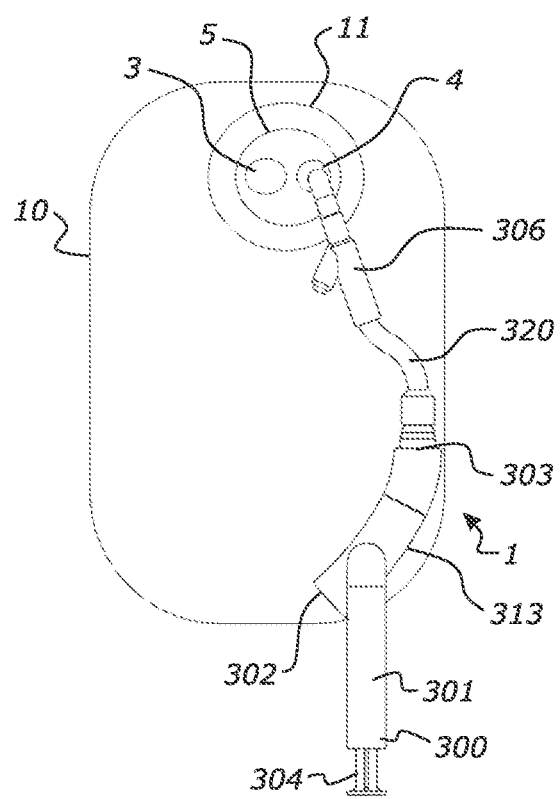

NUTRIENT RECYCLING DEVICE

FIELD OF THE INVENTION

The present invention relates to a nutrient recycling device. More particularly, but not exclusively, it relates to a nutrient recycling device for gastrointestinal stomas and fistulas.

BACKGROUND OF THE INVENTION

Colorectal cancer is a cancer which develops from the colon or rectum and is currently the third most prevalent cancer worldwide. Ileostomies remain a cornerstone of colorectal cancer management, particularly for rectal cancer management. Ileostomy involves dividing the ileum (the distal small bowel) and bringing one or both ends onto the skin of a patient so that digestive contents can flow into a stoma bag. Traditionally, the digestive contents bypass the colon and are collected in the stoma bag and then emptied manually.

Loop ileostomy is a common type of ileostomy which is intended to temporarily divert digestive contents, while the gastrointestinal tract distal to the ileum heals after colorectal surgery. It is usually intended that the loop ileostomy will be reversed by reconnecting the divided ends of the bowel back together, once healing has occurred. A radiological test is usually performed before the reversal surgery, to confirm that healing has occurred and that the bowel is not leaking. Usually a patient requires at least 1-2 weeks for their gastrointestinal tract distal to the ileum to heal sufficiently to perform a radiological leak test and consider reversal surgery.

After a leak test, some patients may have an "early reversal" of their ileostomy, performed within 1-2 weeks after surgery.

However, it is more usual for ileostomy reversal surgery to occur around 6-12 weeks after surgery. It is generally not considered to be safe to perform the reversal surgery between 2-6 weeks after surgery, because of the presence of internal adhesions that increase surgical risk. If a patient is having chemotherapy, they may need to retain an ileostomy for many months until the chemotherapy is finished, before surgery can be safely performed.

As digestive contents are evacuated from the patient's body, patients may suffer from fluid, electrolyte and nutrient losses as ileostomy bypasses the colon which resorbs water, electrolytes and certain nutrients. As a result, patients may experience dehydration and subsequent renal injury, and may need to be readmitted to hospital for management with intravenous fluid replacement. Some patients have "high output" ileostomies, being at increased risk of dehydration and renal injury, and may therefore need to be additionally managed with medications that slow gut transit, and with oral rehydration solutions that may be poorly tolerated. Stoma patients often use a lot of hospital resources due to the additional management required, and the related readmissions due to stoma-related dehydration.

Ileostomy patients having chemotherapy, may also suffer excessive stoma output during chemotherapy, which leads to dose reductions and suboptimal therapy. Leaving the colon without any internal nutrients for an extended duration may also increase the risk of "anterior resection syndrome", which is poor bowel function after rectal cancer surgery. Anterior resection syndrome is associated with a poorer quality of life in colorectal cancer survivors.

When an ileostomy is reversed, patients may experience ileus (slow recovery of gut function), partly due to the poor condition of the gut distal to the ileostomy due to the lack of nutrition. A loop ileostomy also depletes the bacterial microbiome that normally occupies the colon, which contributes to colonic health, and as a result, patients who undergo reversal surgery may experience *Clostridium difficile* infections. *Clostridium difficile* infections prolong hospital stay, can cause serious illness, and may require additional treatments such as antibiotics, surgery or fecal transplants.

Another group of patients who may require a stoma bag are patients with enterocutaneous fistulas, which is an abnormal connection between the gut and the skin. An enterocutaneous fistula may arise as a complication of surgery, or due to a traumatic injury, or because of another disease process such as inflammatory bowel disease. Some neonates may get enterocutaneous fistulas or stomas because of a disease called necrotising enterocolitis, where a segment of gut becomes necrotic.

A type of stoma bag is usually placed over the enterocutaneous fistula to catch the digestive contents. Patients with fistulas often experience poor nutrition, and may become dependent on supplementary feeding such as parenteral nutrition, which is given through a vein. Parenteral nutrition is usually an expensive and risky treatment due to the possibilities of line infections and liver damage.

Furthermore, patients generally dislike having to wear and manage a stoma bag and the associated waste contents. Patients may also need to wake overnight to empty their ileostomies, disrupting sleep patterns. It may be desirable to make waste management of the stoma bag easier for patients, careers and medical practitioners.

Short bowel syndrome is another gastrointestinal related disorder which affects many patients. These are patients who have a short functional gut length due to disease or surgery. Patients with short bowel syndrome usually suffer from malnutrition, dehydration and/or diarrhoea due to a reduction of functioning gut length.

To increase the intake of nutrients, many patients with short bowel syndrome are dependent on IV therapy or parenteral nutrition. These solutions are often expensive, as they use up hospital resources, or when these solutions are administered at home, there is some risk to the patient. It may be desirable to provide an improved or alternative solution to increase the absorption of nutrients in a patient with short bowel syndrome.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

For the purpose of this specification, where method steps are described in sequence, the sequence does not necessarily mean that the steps are to be chronologically ordered in that sequence, unless there is no other logical manner of interpreting the sequence.

It is an object of the present invention to provide a nutrient recycling device which overcomes or at least partially ameliorates some of the abovementioned disadvantages or which at least provides the public with a useful choice.

BRIEF DESCRIPTION OF THE INVENTION

According to one aspect, a nutrient recycling device comprises a flexible bag including a first bag opening and adapted to receive digestive contents from a first surgically created gastrointestinal tract opening through the first bag opening, a pump located within the flexible bag, or incorporated with the flexible bag by attachment to the flexible bag, the pump adapted to pump digestive contents received by the flexible bag to a second gastrointestinal tract opening, and a pump actuator separable from the pump and adapted to be operably coupled to the pump, wherein the pump comprises a pump inlet in fluid communication with an interior of the flexible bag, and a pump outlet connected to an outlet conduit, and wherein the outlet conduit comprises a first portion and a second portion, the first portion of the outlet conduit is located within the bag, and the second portion of the outlet conduit is located externally to the bag and adapted to be insertable into a gastrointestinal tract.

In another aspect, a nutrient recycling device comprises a flexible bag including a first bag opening and adapted to receive digestive contents from a first surgically created gastrointestinal tract opening through the first bag opening, a pump located within the flexible bag and adapted to pump digestive contents received by the flexible bag to a second gastrointestinal tract opening, and a pump actuator separable from the pump and adapted to be operably coupled to the pump, wherein the pump comprises a pump body and an impeller drivable by the pump actuator by a drive coupling between said pump actuator and said impeller, a pump inlet in fluid communication with an interior of the flexible bag, and a pump outlet connected to the outlet conduit.

In yet another aspect, a nutrient recycling device comprises a flexible bag including a first bag opening and adapted to receive digestive contents from a first surgically created gastrointestinal tract opening through the first bag opening, a pump located within the flexible bag, or incorporated with the flexible bag by attachment to the flexible bag, the pump adapted to pump digestive contents received by the flexible bag to a second gastrointestinal tract opening, and a pump actuator separable from the pump comprising a syringe plunger external to the flexible bag and adapted to be operably coupled to the pump to push digestive contents towards the second gastrointestinal tract opening, wherein the pump comprises a pump inlet in fluid communication with an interior of the flexible bag, and a pump outlet connected to the outlet conduit.

In a further aspect, a method comprises receiving digestive contents from a first surgically created gastrointestinal tract opening and pumping the digestive contents to a second gastrointestinal tract opening using a device comprising a flexible bag adapted to receive digestive contents from the first surgically created gastrointestinal tract opening through a first bag opening of the flexible bag, a pump located within the flexible bag adapted to pump digestive contents received by the flexible bag to a second gastrointestinal tract opening, and an outlet conduit adapted to define a flow pathway for digestive content to flow from the pump to the second gastrointestinal tract opening, and a pump actuator separable from the pump and adapted to be operably coupled to the pump, wherein the pump comprises a pump body and an impeller drivable by the pump actuator by a drive coupling between said pump actuator and said impeller, a pump inlet in fluid communication with an interior of the flexible bag, and a pump outlet connected to the outlet conduit, wherein the method further includes positioning the first bag opening over the first gastrointestinal tract opening or over the first and second gastrointestinal tract openings, and operating the device periodically to pump the digestive contents towards the second gastrointestinal tract opening.

According to another aspect the invention broadly comprises a nutrient recycling device configured to collect digestive contents from a first opening of a gastrointestinal tract and recycle the digestive contents to a second gastrointestinal tract opening comprising:
    a bag adapted to receive the digestive contents from the first opening, the bag comprises at least a first bag opening,
    a pump incorporated with the bag adapted to pump the digestive contents to the second gastrointestinal tract opening, the pump comprising:
        an inlet in fluid communication with the interior of the bag, and
        an outlet connected to an outlet conduit adapted to provide a flow pathway for the digestive content to flow from the pump to the second gastrointestinal tract opening.

According to another aspect the first bag opening is configured to be positioned over the first openings of the gastrointestinal tract.

According to another aspect the first bag opening is configured to be positioned over the first and second openings of the gastrointestinal tract.

According to another aspect the first bag opening is configured to be positioned over the first opening, and a second bag opening is configured to be positioned over the second opening of the gastrointestinal tract.

According to another aspect the area of the first and/or second bag opening is configured to be larger than a corresponding opening of the gastrointestinal tract.

According to another aspect the device further comprises a drainage bag opening configured to provide an outlet to empty digestive contents from the bag.

According to another aspect the drainage bag opening is located at or towards the lower end of the bag.

According to another aspect the drainage bag opening is sealed using a releaseable sealing mechanism such as a clip, Velcro, or reversible adhesive.

According to another aspect a lower end of the bag can be rolled over itself to close the drainage bag opening.

According to another aspect the bag comprises an attachment portion configured to attach the bag to a patient.

According to another aspect the attachment portion is located at an exterior sidewall of the bag.

According to another aspect the attachment portion is an adhesive backing.

According to another aspect the adhesive is located around a perimeter of the first bag opening.

According to another aspect the attachment portion is separable from the bag.

According to another aspect the bag is a stoma bag comprising a flexible material.

According to another aspect the pump is located inside the bag.

According to another aspect the pump freely floats or partially floats in the bag.

According to another aspect the pump is located external to the bag.

According to another aspect the bag comprises one or more one-way valves or closing mechanisms to prevent leakage of digestive contents from within the bag.

According to another aspect the stoma bag further comprises at least one external conduit opening adapted to allow at least one external conduit to communicate between the inside and outside of the bag.

According to another aspect the pump housing forms at least part of the bag wall.

According to another aspect the pump is attached to the bag.

According to another aspect the pump is attached to the bag by clips, clasps, buckles, Velcro, zip, slide fastener, snap fasteners, magnets or the like.

According to another aspect the bag comprises a pouch adapted to locate the pump.

According to another aspect the pouch is incorporated into a side wall of the bag.

According to another aspect the pouch comprises a pouch opening to allow fluid communication between the digestive contents and the pump.

According to another aspect the pump is located towards a lower end of the bag.

According to another aspect the outlet conduit comprises a first portion and a second portion, wherein
  a first portion of the outlet conduit is located within the bag, and
  a second portion of the outlet conduit is located external to the bag, the second portion of the conduit adapted to be inserted into the gastrointestinal tract through the second opening of the gastrointestinal tract.

According to another aspect the outlet conduit comprises a one way valve to preclude backflow of digestive content.

According to another aspect the second portion of the outlet conduit comprises one or more apertures on a sidewall configured to allow fluid communication of the digestive contents with the gastrointestinal tract.

According to another aspect the second portion of the outlet conduit comprises an inflatable cuff configured to stabilise the conduit in the gastrointestinal tract.

According to another aspect the first opening is configured to allow inflow of digestive contents into the bag and the digestive contents is collected towards the bottom of the bag due to gravity.

According to another aspect a delivery catheter extends from the bag into the second gastrointestinal tract opening.

According to another aspect the delivery catheter includes an output end positioned downstream in the gastrointestinal tract from the first opening and is configured to reintroduce the digestive contents back into a patient.

According to another aspect the delivery catheter includes an output end positioned upstream from the first opening and is configured to reintroduce the digestive contents back into a patient.

According to another aspect the delivery catheter is inserted through the nasal cavity of a patient.

According to another aspect the delivery catheter is inserted through the skin and inserted into a sidewall of the gastrointestinal tract.

According to another aspect the delivery catheter is inserted back upstream through the first opening of the gastrointestinal tract.

According to another aspect the delivery catheter includes an anchor configured to keep the delivery catheter in a desired region of the small intestines.

According to another aspect the device further comprises an inlet conduit configured to guide digestive content from the first opening to or towards the pump.

According to another aspect the device further comprises a flange configured to stabilise the outlet conduit and prevent the first portion of the outlet conduit from migrating further into the gastrointestinal tract.

According to another aspect the flange is located external to the gastrointestinal tract.

According to another aspect the flange comprises an elbow configured to guide the first portion of the outlet conduit towards the bottom of the stoma bag.

According to another aspect the elbow is low-profile and is rigid.

According to another aspect the pump comprises a body and an impeller.

According to another aspect the impeller is driven by a pump actuator.

According to another aspect the impeller is driven by a magnetic coupling between said pump actuator and said impeller.

According to another aspect the pump is located inside the bag and the pump actuator is located external to the bag.

According to another aspect the impeller includes a magnetic or ferromagnetic element.

According to another aspect the impeller is driven by a mechanical coupling between said pump actuator and said impeller.

According to another aspect the pump is a peristaltic pump.

According to another aspect the peristaltic pump comprises:
  a pump conduit, and
  rollers configured to compress the pump conduit to drive the digestive contents through the pump conduit.

According to another aspect the pump comprises a housing configured to limit entry of large partially digested matter to interior portion of the pump.

According to another aspect the pump actuator is integrated with the pump.

According to another aspect the pump comprises a syringe configured to push the digestive contents towards the second opening of the gastrointestinal tract.

According to another aspect the syringe comprises a plunger external to the bag.

According to another aspect the pump comprises one or more one-way valves.

According to another aspect the pump actively grinds or cuts the digestive content into smaller particles.

According to another aspect the pump actuator is incorporated with the bag.

According to another aspect the pump actuator is located inside the bag.

According to another aspect the pump is located external to the bag.

According to another aspect the pump actuator forms at least part of the bag wall.

According to another aspect the pump actuator is attached to the bag.

According to another aspect the pump actuator is attached by clips, clasps, buckles, Velcro, zip, slide fastener, snap fasteners, magnets.

According to another aspect the bag comprises a pouch adapted to locate the pump actuator in close proximity to the pump.

According to another aspect the pump actuator is adhered to a sidewall of the bag by plastic welding, chemical adhesion or similar adhesion means.

According to another aspect the device further comprises a flow meter configured to measure the flow of digestive contents.

According to another aspect the pump comprises a controller to increase or decrease the flow rate of the digestive contents.

According to another aspect the controller is adapted to be operated manually by a patient.

According to another aspect the controller operates automatically.

According to another aspect the controller operates the pump at set intervals.

According to another aspect the controller operates the pump approximately every 30 minutes to 6 hours.

According to another aspect the controller operates the pump for approximately 30 seconds to 20 minutes at a time.

According to another aspect the controller operates when a predetermined fluid level, bag weight, or bacteria level as detected by a sensor is reached.

According to another aspect the pump operates in a reverse direction to clear blockages.

According to another aspect the operate operates in the reverse direction from time to time to clear blockages.

According to another aspect the pump operates in a reverse direction when a sensor detects a predetermined condition to clear blockages.

According to another aspect the pump alternates between a forward direction and a reverse direction to clear blockages.

According to another aspect the pump comprises at least a section of the bag configured to be externally compressed by a patient to pump said digestive contents along a flow pathway from or near the first bag opening to said second gastrointestinal tract opening.

According to another aspect the invention comprises a nutrient recycling device configured to collect digestive contents from a first opening of a gastrointestinal tract and recycle the digestive contents to a second gastrointestinal tract opening comprising:
 a bag adapted to receive the digestive contents from the first opening, the bag comprises at least a first bag opening,
 a pump comprising:
  at least a section of the bag configured to be externally compressed by a patient to pump digestive contents along a flow pathway from or near the first bag opening towards a second gastrointestinal tract opening,
  a pathway inlet configured receive said digestive content from the first bag opening, and
  a pathway outlet connected to an outlet conduit at a junction, said outlet conduit adapted to provide a flow pathway for the digestive content to flow from the bag to the second gastrointestinal tract opening.

According to another aspect the junction between the pathway outlet and the outlet conduit is located within the bag.

According to another aspect the device further comprises an internal funnel converging from the pathway outlet towards the outlet conduit.

According to another aspect the funnel comprises a wide inlet located upstream the outlet conduit, configured to receive the digestive content.

According to another aspect the funnel is formed at least partially by welding opposing side walls of the bag.

According to another aspect the funnel is a separate component adhered to side walls of the bag.

According to another aspect the digestive contents are driven from an area of high pressure created by the compression of the bag to an area of lower pressure towards the outlet conduit.

According to another aspect the bag comprises:
 a first region configured to receive the digestive contents from the first opening of a gastrointestinal tract, and
 a second region configured to provide a pathway to the outlet conduit.

According to another aspect the bag comprises a doughnut-shape including:
 an aperture through the bag configured to separate the first region and second region of the bag, and
 define a sealed pathway around the perimeter of said aperture.

According to another aspect the aperture is located below the first opening of the gastrointestinal tract.

According to another aspect opposite internal side walls along a longitudinal axis of the bag are joined together to separate the first region and second region.

According to another aspect the bag comprises a U-shape.

According to another aspect the bag comprises a tapered lower region configured to allow the patient to drive the digestive content more efficiently.

According to another aspect the bag comprises a clip configured to compress a segment of the bag, wherein the clip separates the bag into an upstream region and a downstream region, configured to limit flow from travelling upstream of the clip.

According to another aspect the bag comprises a clip configured to fit the aperture through the bag.

According to another aspect the clip is removably attached to the bag.

According to another aspect the device comprises a compression aid configured to drive digestive contents to or towards the outlet conduit.

According to another aspect the compression aid is configured to apply pressure across an entire width of said pathway urging the bag walls together and to slide along the bag to drive the digestive contents to or towards the outlet conduit.

According to another aspect the bag comprises a filter configured to separate fine digestive contents from larger particulate matter.

According to another aspect the filter is located in the bottom region of the bag where digested matter is generally collected.

According to another aspect the filter is located in an upper first region of the bag, towards the first gastrointestinal tract opening.

According to another aspect the bag comprises a sealed section configured to direct the digestive contents to a first region of the bag.

According to another aspect the invention broadly comprises a method of recycling digestive nutrients to collect digestive contents from a first opening of a gastrointestinal tract and recycle the digestive contents to a second opening comprising:
 providing a nutrient recycling device
 positioning the first bag opening over the first and second openings of the gastrointestinal tract,
 running the device from time to time to pump the digestive contents towards the second opening of the gastrointestinal tract.

According to another aspect a patient holds a pump actuator in close proximity to the pump in order for coupling between the pump actuator and pump to drive the pump.

According to another aspect a patient connects a pump actuator to the pump in order for coupling between the pump actuator and pump to drive the pump.

According to another aspect the pump is manually operated by a patient or a caregiver.

According to another aspect the pump operates automatically.

According to another aspect the pump operates at set intervals.

According to another aspect the pump operates approximately every 30 minutes to 6 hours.

According to another aspect the pump operates for approximately 30 seconds to 20 minutes at a time.

According to another aspect the invention broadly comprises a method of recycling digestive nutrients to collect digestive contents from a first opening of a gastrointestinal tract and recycle the digestive contents to a second opening comprising:
 providing a nutrient recycling device
  positioning the first bag opening over the first or first and second openings of the gastrointestinal tract,
  compressing at least a section of the bag to drive the digestive contents along said pathway towards the outlet conduit.

According to another aspect the digestive contents are driven towards the outlet conduit by a patient in a sliding motion.

According to another aspect the digestive contents are driven towards the outlet conduit by a patient compressing the bag repetitively.

According to another aspect each successive compression is located closer towards the outlet conduit.

According to another aspect a clip is externally attached to the bag.

According to another aspect the clip is removed once the bag has been emptied.

According to another aspect the outlet conduit is connected to a second conduit located in the second gastrointestinal tract opening.

According to another aspect the outlet conduit is disconnected from the second conduit to allow replacement or maintenance of the device.

According to another aspect the invention broadly comprises a method of recycling digestive nutrients to collect digestive contents from a first opening of a gastrointestinal tract and recycle the digestive contents to a second opening comprising:
 providing a nutrient recycling device,
 positioning the first bag opening over the first opening of the gastrointestinal tract,
 collecting digestive contents in the bag, and
 pumping the collected digestive contents from the bag through the output end of the delivery catheter to a location upstream of the first opening of the gastrointestinal tract.

According to another aspect the digestive contents pass through the same flow pathway between the output end and the first opening of the gastrointestinal tract a plurality of times to increase absorption.

According to another aspect a delivery catheter is directed from the nose to the upstream location.

According to another aspect a delivery catheter is inserted back upstream through the upstream location.

According to another aspect a delivery catheter is connected through a patient's skin and into a sidewall of the gastrointestinal tract at the upstream location.

According to another aspect a patient holds a pump actuator in close proximity to the pump in order for coupling between the pump actuator and pump to drive the pump.

According to another aspect a patient connects a pump actuator to the pump in order for coupling between the pump actuator and pump to drive the pump.

According to another aspect the pump is manually operated by a patient or a caregiver.

According to another aspect the pump operates automatically.

According to another aspect the pump operates at set intervals.

According to another aspect the pump operates approximately every 30 minutes to 6 hours.

According to another aspect the pump operates for approximately 30 seconds to 20 minutes at a time.

According to another aspect the pump is automated according to a programmable schedule tailored to each patient's needs.

According to another aspect the invention broadly comprises a kit of parts for constructing a nutrient recycling device according to the previous device clauses, wherein the kit comprises:
 a bag adapted to receive digestive contents from a first opening of a gastrointestinal tract, the bag comprises at least a first bag opening,
 a pump adapted to pump the digestive contents to a second opening of the gastrointestinal tract,
 an outlet conduit adapted to provide a flow pathway for the digestive content to flow from the pump to the second opening of the gastrointestinal tract.

According to another aspect the kit further comprises a pump actuator.

Other aspects of the invention may become apparent from the following description which is given by way of example only and with reference to the accompanying drawings.

As used herein the term "and/or" means "and" or "or", or both.

As used herein "(s)" following a noun means the plural and/or singular forms of the noun.

The term "comprising" as used in this specification and claims means "consisting at least in part of". When interpreting statements in this specification and claims which include that term, the features, prefaced by that term in each statement, all need to be present but other features can also be present. Related terms such as "comprise" and "comprised" are to be interpreted in the same manner.

BRIEF DESCRIPTION OF THE DRAWINGS

The invention will now be described by way of example only and with reference to the drawings in which:

FIG. 6 shows a schematic of a nutrient recycling device with a peristaltic pump.

FIG. 7 shows a schematic of a nutrient recycling device with a syringe pump.

DETAILED DESCRIPTION OF PREFERRED EMBODIMENTS

Figure 1:
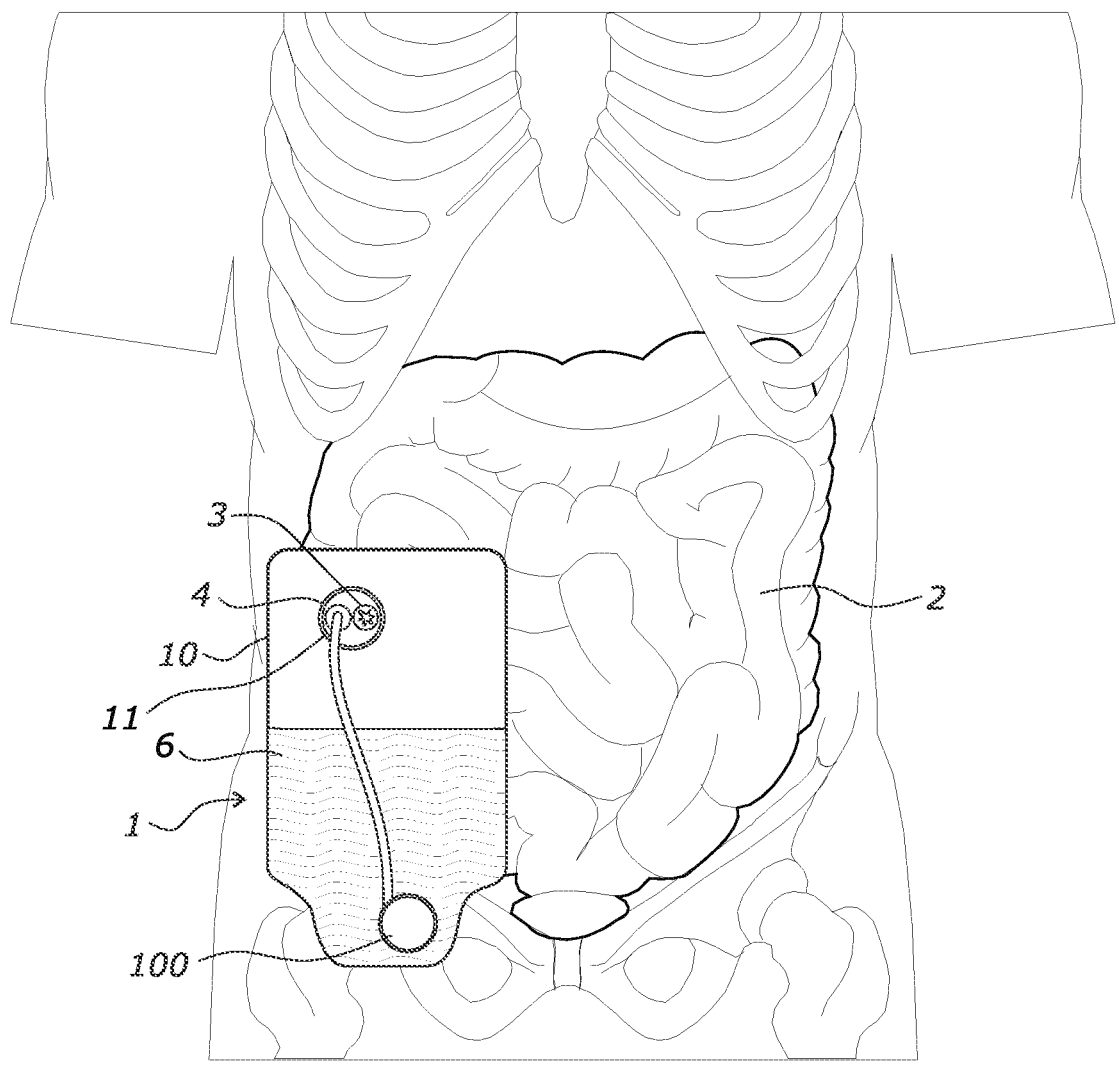
FIG. 1 shows a schematic of a patient and the nutrient recycling device.

With reference to FIGS. 1-10B there is shown a nutrient recycling device 1 configured to collect and recycle digestive contents 6 from the small intestine 2 of a patient.

Preferably, the nutrient recycling device 1 recycles digestive contents 6 from a first opening 3 of the gastrointestinal tract to a second gastrointestinal tract opening 4. Preferably, the nutrient recycling device 1 recycles the digestive contents 6 by collecting the digestive contents 6 in the device 1 and pumping the digestive contents 6 towards the second opening 4.

In some configurations, the digestive contents 6 are recycled from a first opening 3 in the gastrointestinal tract to a second downstream opening 4 in the patient. In other configurations, the digestive contents 6 are recycled from a first opening 3 in the gastrointestinal tract to an upstream location in the patients gastrointestinal tract.

In some configurations, the first opening is the proximal opening 3 of the ileum 2 (distal small bowel). Preferably the second opening is a distal opening 4 of the ileum 2. In this configuration, the digestive contents 6 are recycled downstream from the first opening 3. The device 1 preferably limits fluid and nutrient loss from a stoma 5 as digestive contents 6 are recycled back into the digestive tract. In another configuration, the digestive contents 6 are recycled from the first opening 3 of the gastrointestinal tract to an upstream location. In some configurations the upstream location 4' is at or near the jejunum (middle segment of the small intestine, upstream from the ileum) where absorption occurs. Preferably, the second opening 4 is downstream from the stomach and duodenum.

Figure 10A:
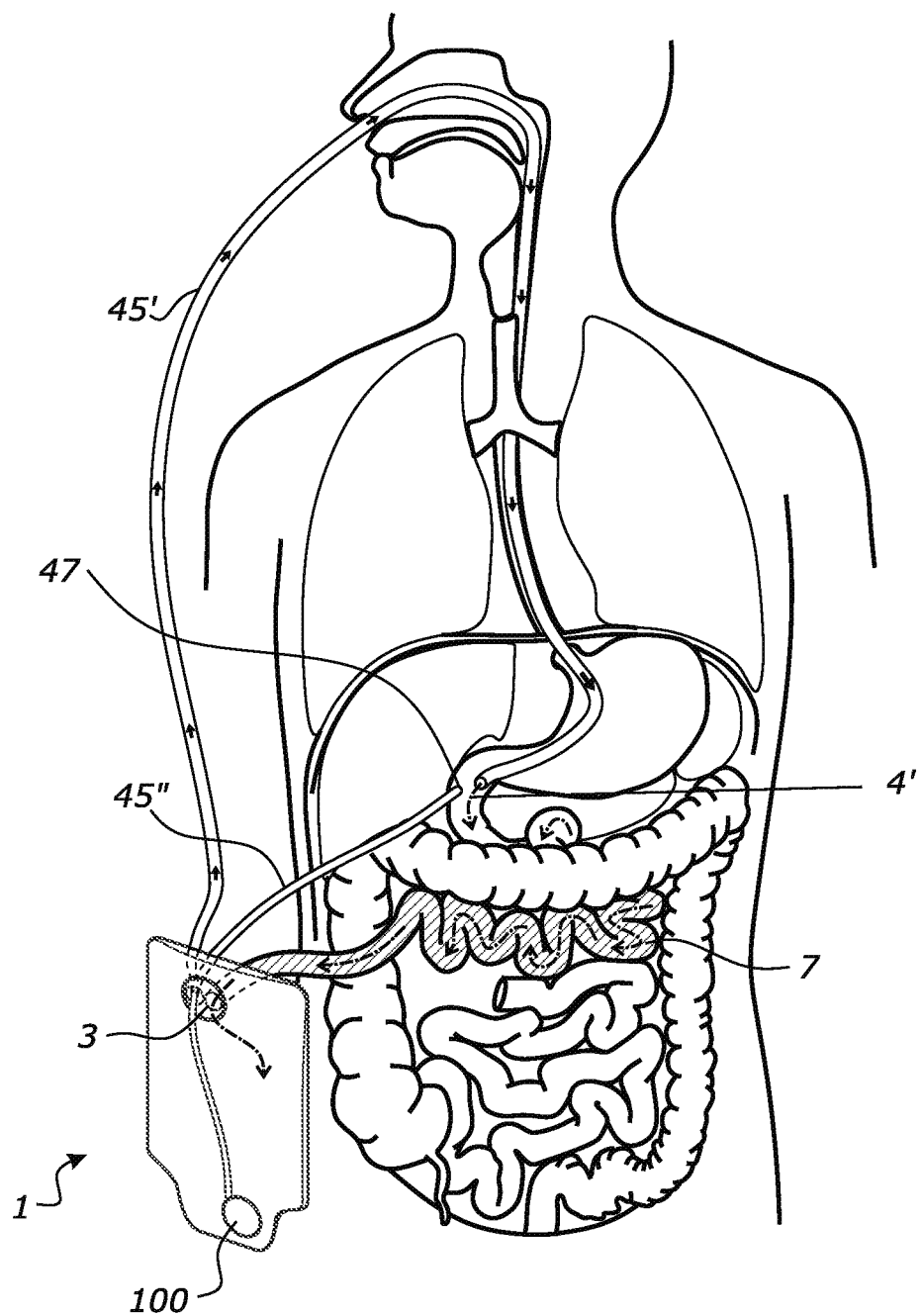
FIG. 10A shows a schematic of a patient and a nutrient recycling device with a delivery tube introduced at different locations.
Figure 10B:
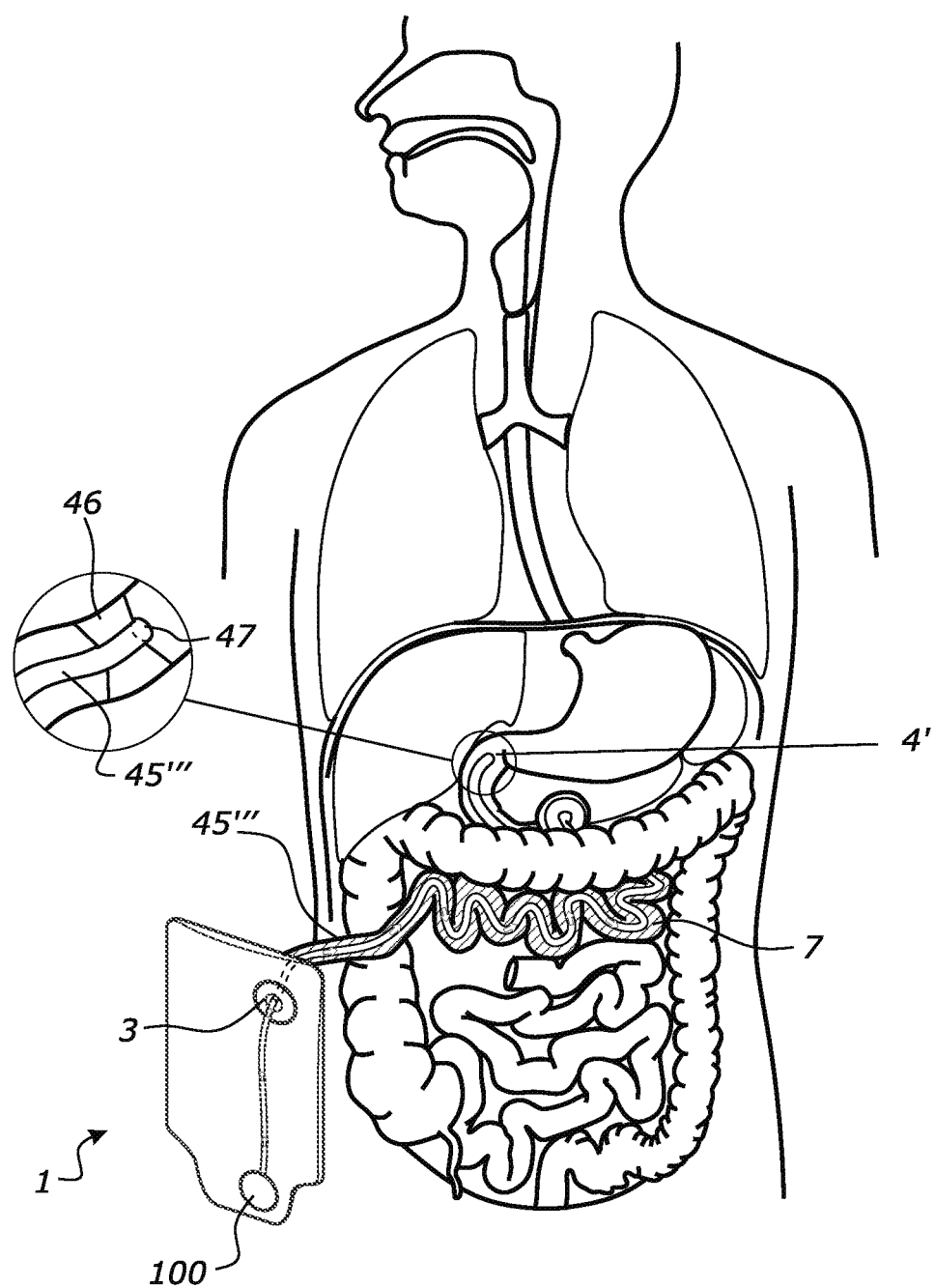
FIG. 10B shows a schematic of a patient and a nutrient recycling device with a delivery tube introduced at another location.

Preferably once the digestive contents 6 exits the upstream gastrointestinal tract location 4', the digestive contents 6 flow naturally, such as by smooth muscle contractions, from the upstream location 4', downstream towards the first opening 3 of the gastrointestinal tract. Recycling digestive contents 6 upstream as described in this configuration means that a particular portion of the gastrointestinal tract can be reused as the digestive contents 6 passes along the same multi-circulation gastrointestinal flow path 7, more than once as shown in FIGS. 10A and 10B (shaded-pattern of the gastrointestinal tract). Preferably, the digestive contents 6 pass through the same flow pathway between the output end 47 and the first opening of the gastrointestinal tract 3 a plurality of times to increase absorption.

Preferably, the multi-circulation gastrointestinal flow path 7 is defined as part of the gastro-intestinal tract between the upstream gastrointestinal tract location 4' to the first gastrointestinal tract opening 3.

It may be advantageous to reuse the same portion of gastrointestinal tract 7 to increase absorption. This desired segment of the gastrointestinal tract is configured to provide a multi-circulation gastrointestinal flow pathway 7 where the digestive contents 6 flow through the flow pathway more than once. Multi-circulation through the same flow pathway 7 in a desired segment of the gastrointestinal tract may increase the time that nutrients are in contact with the gastrointestinal tract wall, and therefore increase the likelihood of nutrients being absorbed by the patient.

Circulating digestive contents 6 over the same multi-circulation gastrointestinal flow pathway 7 effectively increases the length of gastrointestinal tract which the contents pass over, thus increasing likelihood of nutrient absorption. The desired segment of the gastrointestinal tract may function better than other parts or may have specific absorption characteristics (absorbs particular nutrients). Multi-circulation of digestive contents may be beneficial to patients with nutrient absorption disorders such as short bowel syndrome.

Multi-circulation of digestive contents may also be beneficial for improving electrolyte balance in patients with short-gut syndrome. Electrolytes may be secreted in the upper part of the small bowel before fluid absorption occurs effectively. Recirculating the gut contents back to an upstream location 4' (such as at the jejunum) once the intestinal fluid has reached a physiological concentration of electrolytes may improve the net absorption of fluids and electrolytes. Electrolyte deficits such as sodium and magnesium deficiency may be corrected by this treatment.

Multi-circulation of digestive contents in short-gut syndrome may enable patients to reduce their reliance on intravenous (parenteral) forms of supplementary nutrition. Reducing the reliance on parenteral nutrition may lead to other benefits such as reduced infection risk, improved liver health and reduced cost of care.

Advantages of the nutrient recycling device 1 in some configurations may also include reducing or eliminating dehydration and renal impairment due to traditional ileostomy, improving chemotherapy patient survival (by allowing fulfilment of chemotherapy regimens), preventing worse colonic function after surgery caused by deprivation of internal nutrients, preservation of the colonic microbiome, and/or reducing the burden of waste content management associated with stoma bags.

It is also anticipated that the device 1 can be used in other medical procedures requiring recycling of waste or other fluid or partially fluid material. The nutrient recycling device 1 may be used to recycle contents from other portions of the gastrointestinal tract.

For example, the nutrient recycling device 1 may be used to manage gastrointestinal fistulas to reduce malnutrition, fluid and electrolyte imbalance. The benefits of the device 1 in small bowel fistulas may be significant, because fistula patients tend to have very high outputs of gut contents, even if they eat nothing at all. This is because the gut makes several litres of fluid each day (gastric juices, pancreatic fluid, bile, saliva, mucosal secretions), which are progressively absorbed along the way toward the colon. Small bowel fistulas, which are not made intentionally, may be located in the mid or upper small bowel, meaning that up to several litres of fluid may be lost per day. These patients are at very high risk of dehydration and renal injury, and their stomas are typically complex to manage, requiring specialist nursing care. Fistula patients often need to be kept in hospital for management of fluids and stoma bags, in specialist units, and at substantial cost. Fistula patients are also typically at risk of malnutrition due to the lost capacity to absorb food. Fistula patients may also suffer skin damage around the stoma site because small intestine contents are damaging to skin, and they may suffer more frequent bag leaks due to the high outputs putting pressure on the bag seal. Furthermore, the fluid loss and stoma management may be exacerbated by eating, meaning fistula patients may need to be placed nil-by-mouth. Due to the inadequate nutrition, they often need to be given replacement nutrition through a vein—called 'parenteral nutrition', which is expensive and is deemed a risk to the patient due to the possibility of line infections and severe sepsis (can cause death), and some patients experience liver damage. Typically, fistula patients are left in this predicament for many months before it is safe to operate to close their fistulas, sometimes being required to stay in hospital for the duration of this whole period.

In some patients with a fistula, it is possible to access the distal gut through a tube or catheter. It may be desirable to improve nutrition of patients with fistulas by recycling the content from a fistula into the downstream gut.

A recycling device is anticipated to make these problems easier to manage in the certain fistula patients—particularly dehydration, nutrition and stoma cares—and therefore reducing costs.

It is also anticipated that the nutrient recycling device 1 may be used to bypass a segment in the patient's body, by recycling the contents from a first opening 3 and returning the contents to a second opening 4. For example, the device 1 may be useful in other organ systems to control outputs and/or input such as content in the urinary tract.

Stoma Bag and Patient

With reference to FIG. 1, in the most preferred configurations, the nutrient recycling device 1 comprises a pump 100 incorporated with a bag 10, adapted to recycle fluid and nutrients from digestive contents 6 from a first opening 3 of a gastrointestinal tract to a second opening 4 of the gastrointestinal tract. Preferably the bag 10 is a stoma bag. The nutrient recycling device 1 is adapted to be worn externally by a patient.

Preferably, the stoma bag 10 comprises a bag opening 11. In one configuration, the bag opening 11 is preferably positioned over a first opening of the gastrointestinal tract 3. Preferably, the bag opening 11 is positioned over a stoma 5 of a patient. The stoma 5 is an opening on the surface of a patient's abdomen configured to allow access to the first and second opening of the gastrointestinal tract.

Preferably, the area of the bag opening 11 is larger than the corresponding stoma 5 which it fits over. Preferably, the bag opening 11 is located towards an upper end of the stoma bag 10.

The stoma 5 is an opening on the surface of the abdomen, and preferably provides access to the proximal opening 3 and distal opening 4 of the ileum. The preferred flow pathway of the digestive contents 6 is shown by arrows in FIG. 2A. Preferably the proximal opening 3 of the ileum 2 is an inlet and is configured to evacuate the patient's digestive contents 6 into the stoma bag 10. The distal opening 4 of the ileum 2 is preferably an outlet and is configured to receive digestive contents 6 from the stoma bag 10.

In the preferred configuration, the stoma bag 10 comprises an attachment portion. Preferably the attachment portion is located at an exterior sidewall of the stoma bag 10.

Optionally, the attachment portion comprises an adhesive backing to adhere the stoma bag 10 to the skin of a patient. Preferably, the adhesive is located around the perimeter of the bag opening 11.

In one configuration, the attachment portion is integrated with the side wall of the stoma bag 10.

In another configuration, the attachment portion is separable from the stoma bag 10.

In one configuration, the attachment portion remains adhered to the patient, while the stoma bag 10 can be detached and reattached as desired. A separable stoma bag 10 may be advantageous if it is desirable to allow the stoma bag 10 to be removed for replacement, or to attend to the internal components of the stoma bag 10. For example, the stoma bag 10 may be replaced every few days, or as required.

Optionally, the stoma bag 10 comprises a rubber ring on a sidewall, and the attachment portion comprises a complimentary rubber ring adapted to connect and disconnect the stoma bag 10 from the attachment portion. It is anticipated that other connection mechanisms known in the art may be implemented to connect and disconnect the stoma bag 10 from the attachment portion.

Optionally, the nutrient recycling device 1 can be further supported and/or secured to a patient by attaching the stoma bag 10 to a belt or similar article worn by the patient, such as clips, buckles, or straps for example.

In the preferred configurations, the stoma bag 10 comprises a generally rectangular shape. Optionally, the stoma bag 10 comprises an oval-like shape.

Preferably, the stoma bag 10 has a capacity of 500 mL to 2000 mL. In the most preferred configurations, the stoma bag 10 has a capacity of 800 mL to 1200 mL.

Preferably, the stoma bag 10 length is 10 cm to 30 cm long. In the most preferred configurations, the stoma bag 10 length is 12 cm to 20 cm long.

Preferably, the stoma bag width 10 is 10 cm to 25 cm wide. The most preferred configurations, the stoma bag 10 width is 12 cm to 16 cm wide.

It is anticipated the size of the stoma bag 10 may need to be shaped to different custom sizes depending on the configuration of the stomas or fistula opening(s) and the patient's body habitus. For example, larger stoma bags 10 may be necessary for patients with fistulas due to the generally higher output of digestive contents 6.

Preferably, the stoma bag 10 comprises an impermeable plastic, for example polyethylene.

Preferably, the stoma bag 10 comprise a material impermeable to the digestive contents 6. Preferably, the stoma bag 10 also comprises a material impermeable to the odours and other gases from the digestive contents 6.

Preferably, the stoma bag 10 comprises a flexible material. Preferably, the stoma bag 10 can flatten when the bag is not full with digestive contents 6, and swell when digestive contents 6 enter the bag 10. An advantage of a flexible stoma bag 10, is to ensure that the nutrient recycling device 1 is compact. Using a stoma bag may be advantageous, as they are generally inexpensive and can therefore be disposed or replaced after a single or use (or a few uses). A disposable or replaceable stoma bag 10 may be advantageous as a patient or a caregiver does not need to clean the bag 10 between separate uses.

In one configuration, the stoma bag 10 is transparent to reveal the internal contents of the bag 10. In another configuration, the stoma bag 10 is opaque and may be a similar colour to the patient's skin. This may be advantageous if it is desired to conceal the contents of the bag 10, and to make the nutrient recycling device 1 more discrete for the patient to wear.

Optionally, the nutrient recycling device 1 comprises an external cover adapted to be removable or partially removable from the stoma bag 10. In one configuration, the stoma bag 10 is transparent, and the external cover is opaque. For example, the external cover optionally comprises a flap configured to be lifted to reveal the internal contents of the bag 10 such as the digestive contents 6, or the position of the pump 100. Alternatively, the position of the pump 100 may simply be felt by the patient or medical caregiver. Optionally, the external cover is a similar colour to the patient's skin.

Stoma Bag and Pump Connection

The nutrient recycling device 1 in its most preferred configurations comprises a pump 100. The pump 100 is preferably incorporated with the stoma bag 10. In some configurations, the pump 100 is incorporated inside the stoma bag 10. In other configurations, the pump 100 is incorporated external to the stoma bag 10. In yet another configuration, the pump 100 is incorporated with the bag 10 by forming at least part of the wall of the bag. Optionally, the pump 100 is incorporated with the bag 10 by an attachment means.

In some configurations, the nutrient recycling device 1 is configured to pump liquid and partially liquid digestive content 6.

The digestive content 6 preferably enters the stoma bag 10 through the first opening 3 of the gastrointestinal tract and is configured to allow inflow of digestive contents 6 into the bag 10. In the preferred configurations, the digestive content 6 is collected towards the bottom of the stoma bag 10 due to gravity, and the pump 100 is immersed in the digestive contents 6. Preferably, the digestive content 6 enters the bag 10 through natural propulsion of the gastrointestinal tract such as due to smooth muscle contractions.

Optionally, an inlet conduit (not shown) can be configured to guide the digestive content 6 from the proximal opening 3 of the ileum 2 to or towards the pump body 101.

Optionally, medicament can be added into the stoma bag 10 or conduit 20, 30 to be pumped into the distal segment of the gastrointestinal tract. For example, antibiotics such as metronidazole or vancomycin may be used to treat infections such as *Clostridium difficile* infections. Alternatively, probiotics such as beneficial bacterial populations may be introduced to re-establish or alter a patient's colonic microbiome.

Preferably the pump 100 comprises a pump inlet 102 which communicates with the interior of the stoma bag 10. Preferably the pump inlet 102 is in fluid communication with (preferably immersed in) the digestive content 6 in the stoma bag 10.

Preferably, the digestive content 6 is pumped from the pump 100 to the second opening 4 of the gastrointestinal tract. Preferably, the digestive content 6 exits the pump 100 from a pump outlet 103. Preferably the pump 100 is able to drive the digestive contents 6 against gravity.

The connection of the nutrient recycling device 1 to the proximal opening 3 and the distal opening 4 can be established during an ileostomy or other medical procedure.

In some configurations, connecting the nutrient recycling device 1 during the procedure means that the digestive content 6 can be recycled into the distal gastrointestinal tract without further invasive procedures for surgery.

Recycling digestive content 6 to the second opening 4 which is downstream from the first opening 3 soon after the gastrointestinal tract distal to the ileum has healed may be advantageous as this may reduce patient and economic burden of stoma-related dehydration.

Early stimulation of the distal gastrointestinal tract may also reduce the likelihood of renal failure, electrolyte and/or acid-base imbalance which may cause severe illness and slow recovery times.

Furthermore, the nutrient recycling device 1 may reduce the loss of colonic microbiome and decrease the inoperative colon period. The device 1 may decrease the short-term and/or long-term negative effects on bowel function due to ileostomy diversion.

Conduit/Tubing

In the preferred configuration, the nutrient recycling device 1 comprises a conduit 20, 30. Preferably the conduit 20, 30 provides a flow pathway for the digestive content 6 to flow from the pump 100 through to the upstream location 4' in the patient's gastrointestinal tract.

As illustrated in FIGS. 10A and 10B, in some configurations, the nutrient recycling device 1 comprises a delivery catheter 45 which extends to the upstream location 4'. The nutrient recycling device 1 as shown in FIGS. 10A and 10B is shown to be off on a side of the patient for illustrative purposes only so that the internal organs are not covered. When the nutrient recycling device 1 is in use, the bag 10 can be positioned as required for functioning and/or for comfort.

In some configurations, the conduit 30 acts as the delivery catheter 45 and extends from the stoma bag 10 and directly enters the upstream location 4'. In other configurations, the delivery catheter 45 provides an extension from the conduit 30 to extend into the upstream location 4' at the desired location. The desired location in the most preferred configurations is in the small intestine where nutrient absorption in the gastrointestinal system occurs.

In some configurations, the delivery catheter 45 which extends into the upstream location 4' is an enteral feeding tube such as a gastro-jejunal tube. Preferably the delivery catheter 45 is flexible or semi-flexible so it can be directed into the patient and situated in the desired location.

In some configurations, the second opening 4 is located downstream from the first opening 3 in the gastrointestinal tract in a direction towards the anus. In one configuration, the first opening 3 is a proximal stoma, and the second opening 4 is a distal stoma. Preferably, the delivery catheter 45 includes an output end of the delivery catheter 45 which is positioned downstream in the gastrointestinal tract from the first opening 3 configured to reintroduce the digestive contents back into a patient.

In other configurations, the upstream location 4' is located upstream in the gastrointestinal tract from the first opening 3 towards the stomach. The digestive contents 6 contained within the bag 10 of the nutrient recycling device 1 is driven to the upstream location 4' within the gastrointestinal system. As illustrated in FIGS. 10A and 10B, it is anticipated that the delivery catheter 45 can be inserted and navigated to different locations in a patient, so that an output end of the delivery catheter 45 is located in the desired location to reintroduce the digestive contents back into a patient. FIG. 10A shows that the delivery catheter 45', 45" can be provided through the nasal cavity or through the abdomen.

FIG. 10B shows the delivery catheter 45''' can be inserted back through the first opening 3. Preferably, the output end 47 of the delivery catheter 45 is positioned upstream from the first opening 3.

As shown in FIG. 10A, in some configurations, the delivery catheter 45' is inserted through a nasal cavity of the patient. Preferably, the delivery catheter 45' is directed from the nose to the upstream location 4' (upstream from the first opening 3).

In other configurations, the delivery catheter 45" is connected through a patient's skin and into a sidewall of the gastrointestinal tract so that digestive contents 6 can be delivered from the bag 10 back into the gastrointestinal system to the upstream location 4' upstream the first opening 3.

This may typically be performed by connection of the catheter 20 arising from the pump 100 to a delivery catheter 45" which is a percutaneous gastrojejunal feeding tube. Percutaneous gastrojejunal feeding tubes may be placed through the abdominal wall, before passing through the pylorus of the stomach and into the jejunum, providing intermittent or continuous access to the small bowel. The catheter 20 leading from the pump is preferably connected directly to the inlet of a gastrojejunal tube. In some configurations, the gastrojejunostomy tube may be anchored in the stomach across the abdominal wall by the use of a balloon.

In other configurations, the upstream location 4' can be accessed by a percutaneous enterostomy procedure, where a needle is instrumented into the gut through the abdominal wall to provide an access port, such as under imaging or endoscopic guidance.

In yet another configuration as shown in FIG. 10B, the deliver catheter 45''' is inserted back upstream through the first opening 3 of the gastrointestinal tract to the upstream location 4'. In this configuration, the digestive contents 6 first enters the stoma bag 10 through the first opening 3 after passing through a functioning segment of the small intestine. The collected digestive contents 6 are then pumped back upstream through the first opening 3, where the delivery catheter 45''' provides a pathway to the upstream location 4' at the desired upstream location in the gastrointestinal tract.

There may be one or multiple upstream openings to release the digestive content 6 back into the gastrointestinal tract. The digestive contents re-passes through the functioning segment of the small intestine. Re-passing may be undertaken multiple times to increase the time that gut contents are in contact with the lumen to increase overall absorption.

As shown in the schematic at FIG. 10B, in some configurations the delivery catheter 45 includes an anchor 46 configured to keep the delivery catheter 45 in a desired region of the small intestines. Preferably, the anchor 46 is able to resist movement against the natural propulsion of the gastrointestinal tract. Preferably, the digestive contents 6 can flow past the anchor. This may be particularly useful where the delivery catheter 45''' is inserted back upstream into the gastrointestinal tract.

In some configurations, the anchor 46 is inserted into the stomach (not shown), and the delivery catheter 45 is supported from the stomach. Preferably, the anchor includes arms which engage against the stomach wall to hold the delivery tube in place. In some configurations, the anchor comprises a T-shape.

In other configurations, the anchor is a stent or vacuum collar (as shown in FIG. 10) to engage with the inner walls of the gastrointestinal tract to keep the catheter in place. Preferably, the delivery catheter 45 includes perforations or apertures towards the output end of the tube to provide exit paths for the digestive contents 6.

In yet another configuration, the anchor 46 is located at or towards the first opening 3 of the gastrointestinal tract (not shown). Optionally, the anchor is a base plate which engages against the outer surface at the first opening 3 to hold the delivery catheter 45 in place. In another optional configuration, the anchor is a pouch contained inside a stoma bag 10 near to the first opening 3. The delivery tube 45''' extends upwards from the anchor 46 at the first opening 3. It is anticipated that the delivery tube 45 may be introduced into the patient through other pathways to get to the desired location as known by a skilled person in the art.

In some configurations, a first portion of the conduit 20 is located within the stoma bag 10. Preferably, a second portion of the conduit 30 is adapted to be inserted into the distal opening 4 of the ileum 2.

Preferably, the conduit 20, 30 is separable from the stoma bag 10. A separate conduit 20, 30 may be advantageous when a patient changes their stoma bag 10. For example, a portion of the conduit 30 can remain in the distal opening 4 of the ileum 2, while the stoma bag 10 is removed.

Preferably, the diameter of the second portion of the conduit 30 is smaller than the diameter of the second opening 4 in a stretched state. Preferably, the diameter of the conduit 20, 30 is large enough to reduce resistance of flow and/or to reduce the chance of blockages.

In the preferred configuration, the conduit 20, 30 is a continuous conduit comprising a first portion of the conduit 20 and a second portion of the conduit 30.

Figure 3A:
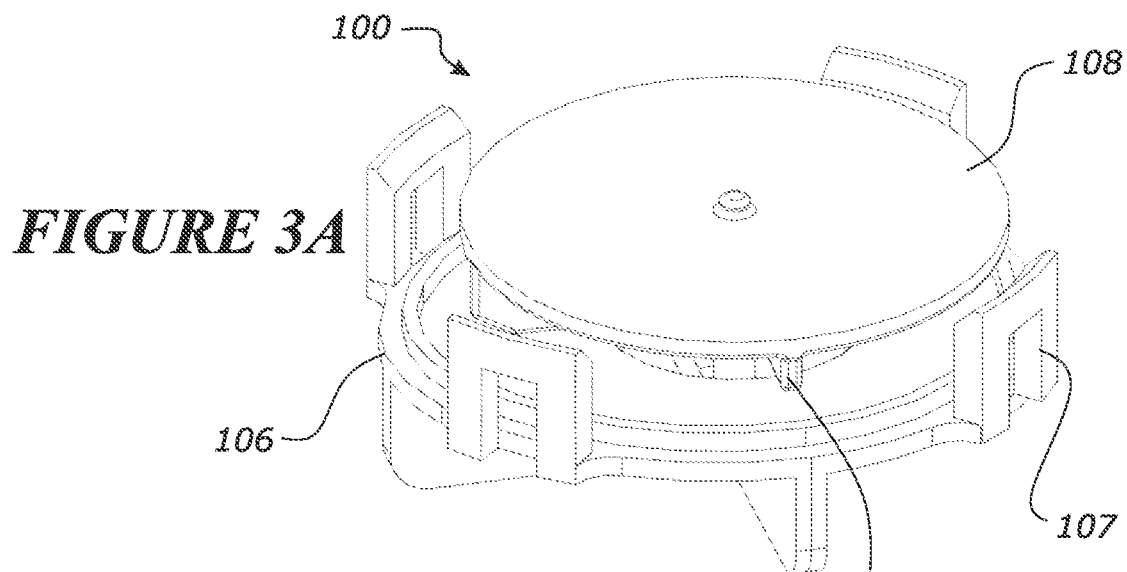
FIG. 3a shows a perspective view of the base and internal components of a pump in the nutrient recycling device.
Figure 3B:
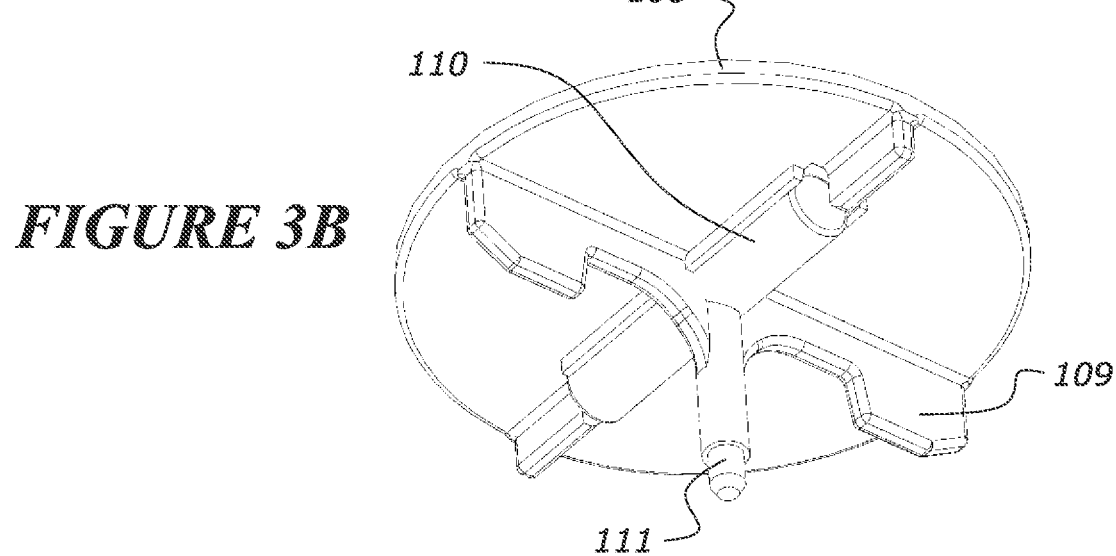
FIG. 3b shows a perspective view of the underside of a movable component in a pump.
Figure 3C:
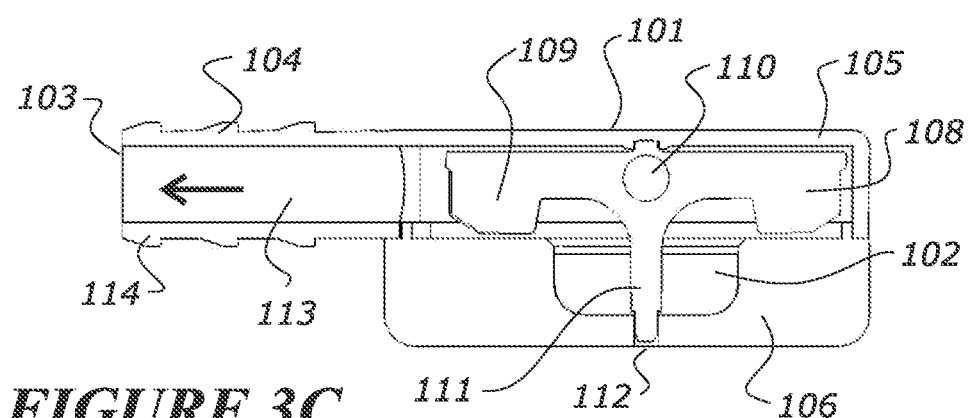
FIG. 3c shows a cross-section of the pump in FIG. 2.

Optionally, the pump 100 comprises ridges 114, as shown in FIG. 3C to engage with a first end 21 of the first portion of the conduit 20.

Preferably, the conduit 20, 30 is hollow. Preferably, the first portion of the conduit 20 conveys the digestive contents 6 from the first end 21 to the second end 22 of the first portion of the conduit 20.

Optionally, the first portion of the conduit 20 comprises a one way valve (not shown) to preclude backflow of digestive content 6 in the first conduit 20.

Optionally, a flange 12 is connected to the conduit 20, 30. Optionally, the flange 12 comprises a rigid material. Preferably, the flange 12 stabilises the conduit 20, 30.

The flange 12 preferably extends radially from the outer sidewall of the conduit 30. Preferably the flange body 12 is located inside the stoma bag 10. Preferably the flange 12 is located external to cavity the second portion of the conduit 30 is inserted into. Preferably the flange prevents the first portion of the conduit 20 from migrating further into the gastrointestinal tract.

Optionally, the flange 12 comprises apertures 17 for suturing the flange to the patient or attaching to a bag.

In one configuration, the flange 12 comprises a circular cross-section.

Figure 2A:
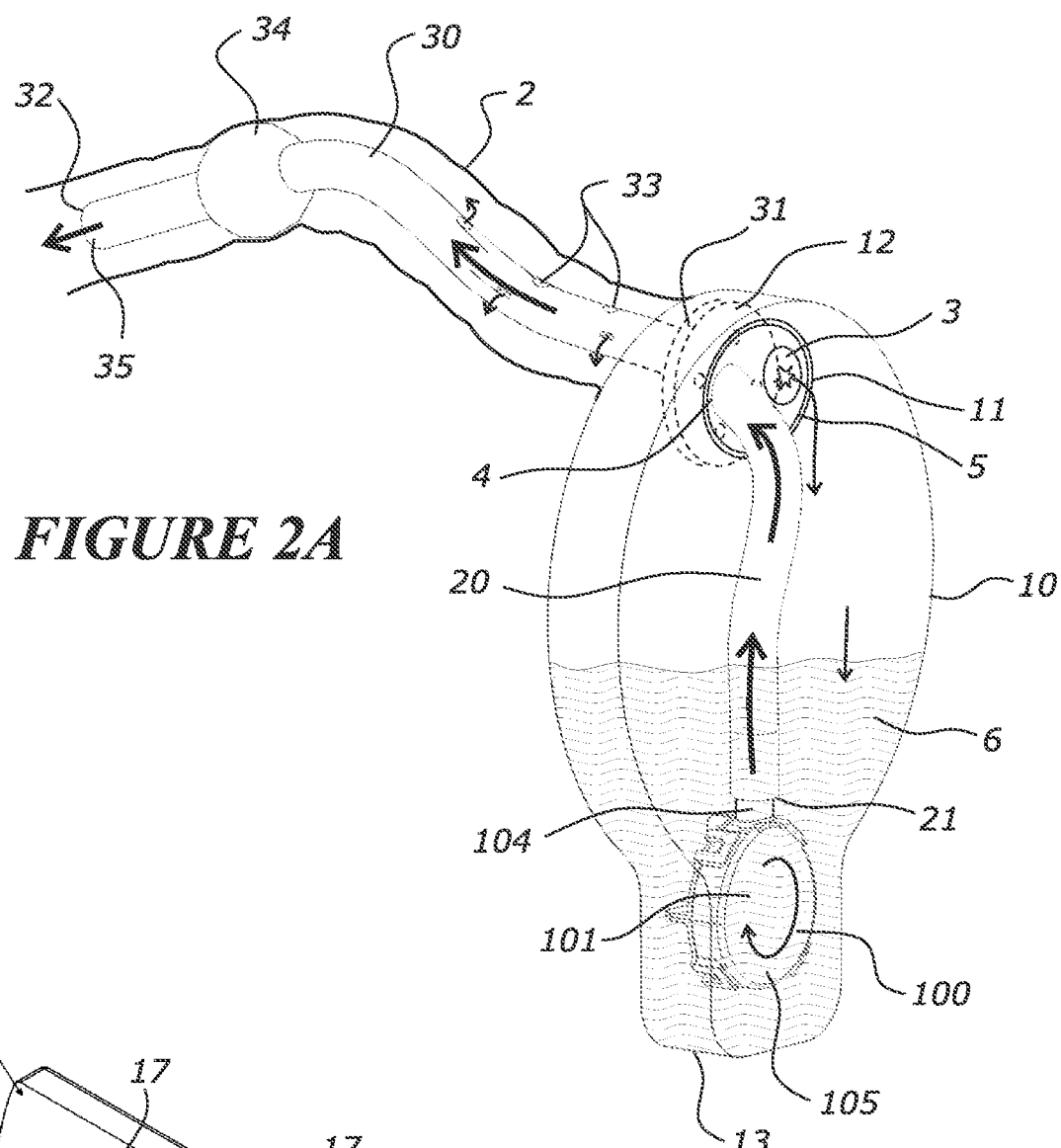
FIG. 2a shows a perspective view of the nutrient recycling device.
Figure 2B:
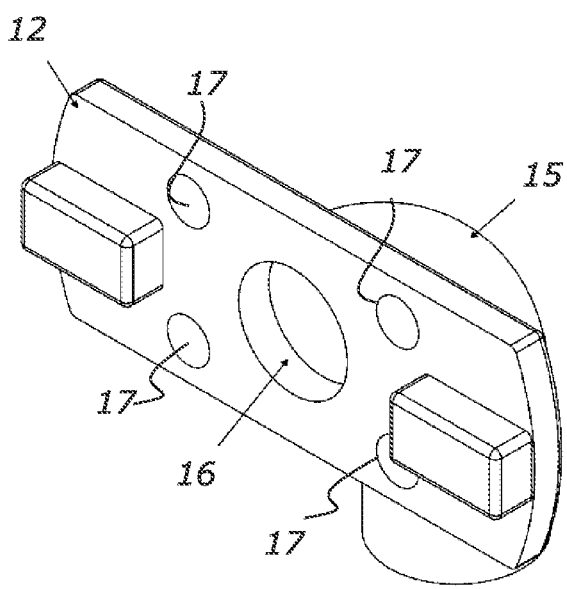
FIG. 2b shows a perspective view of a flange and guiding portion of the device.

In another configuration, the flange 12 comprises a rectangular cross-section as shown in FIG. 2B.

Preferably, the flange 12 comprises an opening 16 configured to receive the conduit 20, 30.

Optionally, the flange 12 comprises an elbow 15 configured to extend into the stoma bag 10. Preferably the flange elbow 15 bends towards the bottom of the stoma bag 10. The conduit 20, 30 is configured to be guided by the elbow 15 towards the bottom of the stoma bag 10. The elbow 15 is preferably rigid. The elbow 15 is preferably low profile.

Figure 4A:
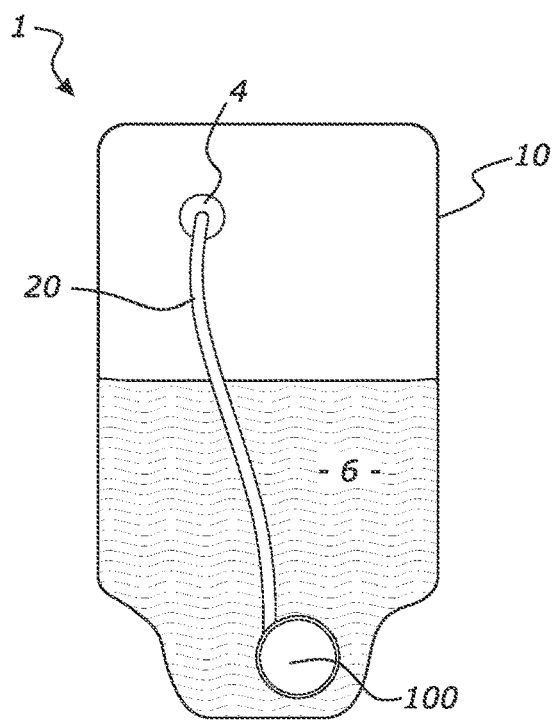
FIG. 4a shows a schematic of the nutrient recycling device with a pump located towards the bottom of the bag.

In the preferred configuration, the length of the first portion of the conduit 20 is adapted to allow the pump 100 to be located towards the bottom of the stoma bag 10 as best shown in FIGS. 2A and 4A. Optionally, the first portion of the conduit 20 is rigid or semi-rigid to locate the pump 100 in the desired position, such as the bottom of the stoma bag 10.

Optionally, the pump 100 comprises a pump connection piece 104. The pump connection piece 104 preferably connects the pump body 101 to a first end 21 of conduit 20.

Optionally the nutrient recycling device 1 comprises a first conduit 20 separate from a second conduit 30. Preferably the first conduit 20 connects the pump 100 to the distal opening 4. Preferably a first end 21 is connected to the pump 100 and a second end 22 is located at the second opening 4. In the preferred configuration, the first conduit 20 is located within the stoma bag 10.

Optionally, the nutrient recycling device 1 comprises a second conduit 30 separate to the first conduit 20. Preferably, the second conduit 30 connects the bag opening 11 to a distal portion of the ileum 2.

Preferably, the second conduit 30 is located external to the stoma bag 10.

The preferred flow pathway of the digestive contents 6 from a first end 31 to a second end 32 of the second conduit 30 is shown by arrows in FIG. 2A.

In the preferred configurations, the first portion of the conduit 20 and the second portion of the conduit 30 comprises the same material. For example, the conduit 20, 30 comprises a medical-grade silicone, however other catheter materials such as polyurethane, PVC or latex rubber are also options.

In other configurations, the first conduit 20 and the second conduit 30 comprises different materials. For example, the first conduit 20 comprises a semi-rigid material to help stabilise the interior components in the stoma bag 10. The second conduit 30 may comprise a more flexible material to help deform to the contour of the ileum 2.

Second Conduit Apertures

In the preferred configurations, the second portion of the conduit 30 comprises one or more apertures 33 on the sidewall of the conduit 30. Preferably, the apertures 33 allow fluid communication of the digestive contents 6 from the second portion of the conduit 30 to the ileum 2.

Preferably, only a small portion of the flowing digestive content 6 exits through the apertures 33. Preferably, the digestive content 6 deposited in this area can be absorbed by the ileum 2.

Preferably the main flow of the digestive contents 6 exists through an outlet 35 at the second end 32 of the second conduit 30. In some configurations all of the flowing digestive content 6 exits through the outlet 35.

The nutrient recycling device 1 preferably limits fluid and nutrient loss from a stoma 5, as digestive contents 6 is recycled back into the gastrointestinal tract.

An advantage of the nutrient recycling device 1 is its ability to reduce some of the common complications of ileostomies. Use of the nutrient recycling device 1 may decrease costs of stoma patients to hospitals due to reduced need for rehydration and other medications and/or readmission to the hospital associated with stomas.

Inflatable Cuff

In the preferred configuration, the second portion of the conduit 30 of the nutrient recycling device 1 comprises an inflatable cuff 34. In the preferred configuration, the inflatable cuff 34 comprises a circular cross-section.

The inflatable cuff 34 preferably operates between a deflated condition and an inflated condition.

In the deflated condition, the inflatable cuff 34 is preferably the same or similar diameter as the second portion of the conduit 30.

In the inflated condition as shown in FIG. 2A, the inflatable cuff 34 comprises a diameter similar to or greater than the diameter of the second portion of the conduit 30. Preferably, in the inflated condition, the inflatable cuff presses against the inner wall of the ileum 2 to stabilise the second conduit 30. The inflatable cuff 34 may help the nutrient recycling device 1 stay the desired position. This may help permit the patient move around in their everyday life without having to worry about the position of the nutrient recycling device 1.

Preferably, the inflatable cuff 34 is located external to the second portion of the conduit 30. Preferably the inflatable cuff 34 in the inflated condition does not decrease to diameter of the conduit 30.

In some configurations, the inflatable cuff 34 can be inflated with saline. Preferably, the saline is delivered by a separate inflating conduit (not shown). Optionally, the inflating conduit can be removed once the second portion of the conduit 30 is secured in the desired location.

Alternatively, the cuff 34 is a vacuum or negative pressure cuff.

In some configurations, an inflating mechanism is integrated with the conduit 30 of the nutrient recycling device 1.

Drainage

In some configurations, the stoma bag 10 comprises a drainage bag opening 13. The drainage bag opening 13 is configured to provide an outlet to empty digestive contents 6 from the stoma bag 10.

Draining the stoma bag 10 may be necessary in the early stages of recovery from colorectal surgery, where the distal gastrointestinal tract is not ready to receive digestive contents 6 yet. The recycling function of the nutrient recycling device 1 may only commence once the patient is recovered sufficiently from the colorectal surgery (usually 1-2 weeks), which is typically confirmed by a radiological leak test of the colorectal join. Optionally, the recycling function of the nutrient recycling device 1 can commence sooner after surgery, for example if stoma output is very high, slightly before the patient is recovered from the colorectal surgery.

Draining the stoma bag 10 may be desired in the later stages of recovery if the medical practitioner wants to recycle some of the digestive contents 6 to the distal gastrointestinal tract, but not all the flow.

Preferably, the drainage bag opening 13 is located at or towards the lower end of the stoma bag 10. In one configuration, the drainage bag opening 13 is a defined outlet at the lower end of the stoma bag 10, for example with a circular cross-section. In other configurations, the drainage bag opening is an opening along the lower end of the stoma bag 10.

In some configurations, the drainage bag opening 13 is adapted to receive the pump 100. For example, the pump 100 may be reinserted through the drainage opening 13 after the patient changes their stoma bag 10.

In the preferred configurations, the drainage bag opening 13 is re-sealable. For example, a clip, Velcro, reversible adhesive, or other releasable sealing mechanisms known to the art may be used. Optionally, the lower end of the stoma bag 10 can be rolled over itself one or more times to close the drainage bag opening, preferably prior to applying this mechanism of clipping or Velcro for example.

Pump Mechanism

In a preferred configuration, the pump 100 of the nutrient recycling device 1 as shown in FIGS. 2A and 3A-C comprises a pump body 101.

The pump 100 preferably blocks or tolerates partially digested particulate matter and avoids clogging of internal parts. Optionally, the pump 100 actively makes the partially digested particulate matter smaller or the digestive contents 6 more fluid. In one configuration, the pump 100 comprises a grinder to make the partially digested particulate matter smaller. In another configuration, the pump 100 comprises one or more blades to cut the partially digested particulate matter into smaller particles.

The pump 100 preferably comprises a housing. In the preferred configuration, the housing comprises a substantially circular cross-section.

In one configuration, the pump 100 comprises a top housing 105. Preferably, the pump 100 also comprises a bottom housing 106. An advantage of the top 105 and bottom housing 106, is to limit larger partially digested particulate matter from entering the interior portion of the pump.

Alternatively, a filter, such as a grate or sieve, incorporated with the housing can limit larger partially digested particulate matter from entering the interior portion of the pump.

Limiting larger partially digested matter can help prevent the pump 100 and/or the conduit 20, 30 from clogging. It may be advantageous to reduce the likelihood of blockages as a blocked conduit 20, 30 may increase resistance or drag in the flow pathway.

In the preferred configurations, the top housing 105 is connected to the bottom housing 106. Optionally, the top housing 105 is separable from the bottom housing 106.

Optionally, the top housing 105 is connected to the bottom housing 106 by fastening members 107 as best shown in FIG. 3A. The fastening members 107 can be a clasp, snap fit mechanism, friction grip mechanism, complementary threaded members or adhesive. It is anticipated that other fastening members known to the art may be used to connect the top housing 105 and the bottom housing 106.

In the preferred configuration, the pump 100 of the nutrient recycling device 1 comprises a movable component 108. In the preferred configuration, the movable component 108 is circular.

Preferably, the movable component 108 is an impeller. Preferably, digestive contents 6 enter the body 101 of the pump 100 through the pump inlet 102. Preferably, the impeller 108 is adapted to be fully or partially immersed in the digestive contents 6 when in use. In the preferred configuration, the nutrient recycling device 1 comprises an inlet 102 located at the base of the bottom casing 106.

The impeller 108 is a rotating component in the pump 100 configured to displace the fluid or partially fluid digestive contents 6. Preferably the inlet 102 is located at or towards the axis of rotation of the pump 100.

Preferably, the impeller 108 comprises fins 109 as shown in FIGS. 3A and 3B to displace the digestive contents 6. Preferably the impeller 108 imparts centrifugal force to the digestive content 6 particles, and drives the digestive content radially outwards towards the inner sidewall of the top housing 105 of the pump. Optionally, the impeller 108 in parts share forces that may shred the digestive contents 6 into smaller particles.

Preferably the fins 109 extend from the underside of the movable component 108. Preferably the fins 109 extend on a plane orthogonal to the plane of the body of the movable component 108.

As the impeller 108 displaces the digestive content 6 in the pump 100, the digestive content 6 is preferably driven from the centre of rotation of the impeller radially outwards.

Preferably, the impeller 108 drives the digestive contents 6 through a flow channel 113 as shown in FIG. 3C. The flow channel 113 preferably leads to the pump outlet 103.

Optionally, the pump 100 comprises a flow channel 113 with increasing area along the flow direction. Preferably, the increased area along the flow channel 113 reduces flow velocity of the digestive content 6 which increases static pressure to help overcome resistance of the pump 100.

Figure 5A:
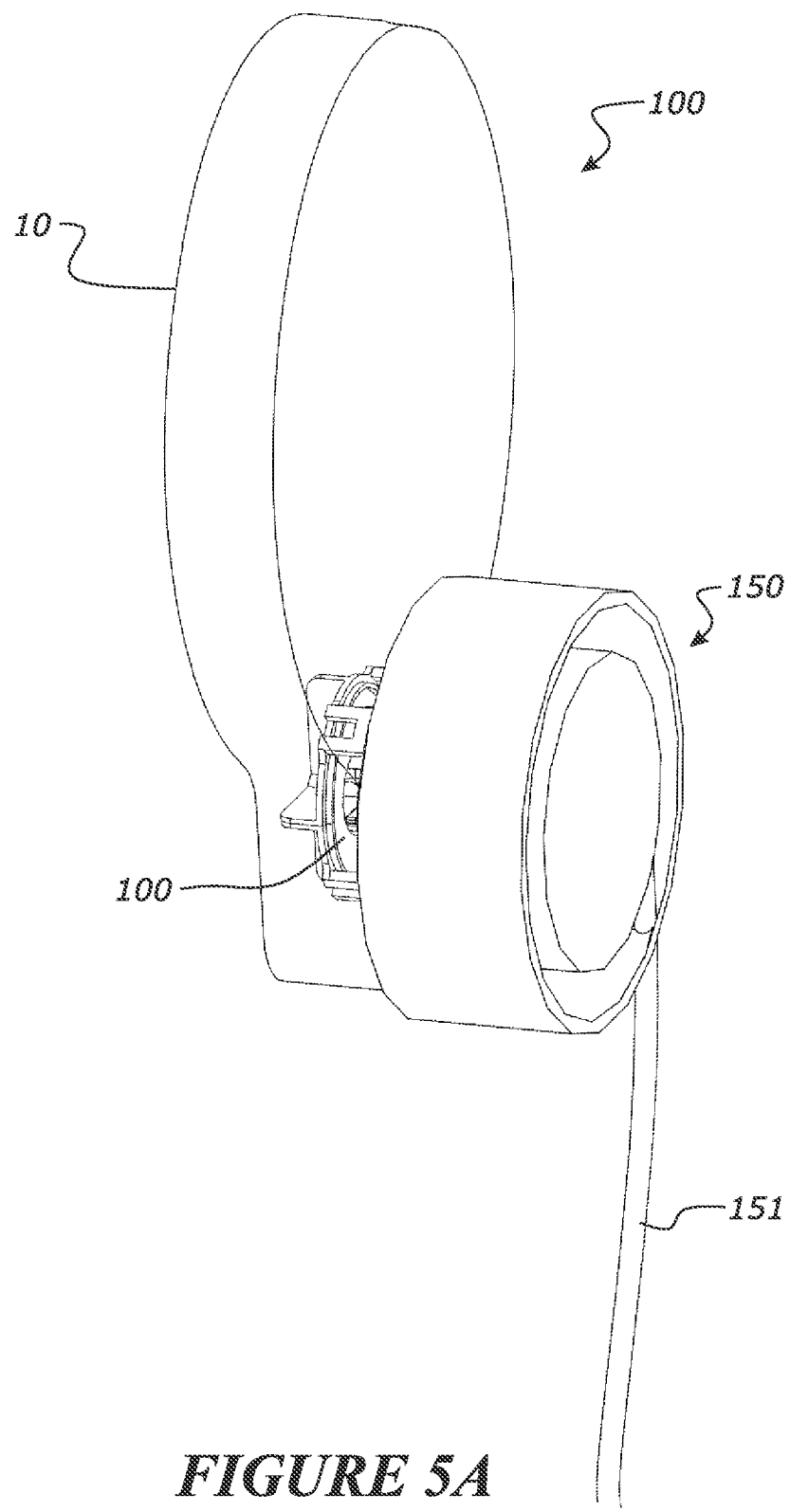
FIG. 5a shows a nutrient recycling device with a complementary pump actuator.
Figure 5B:
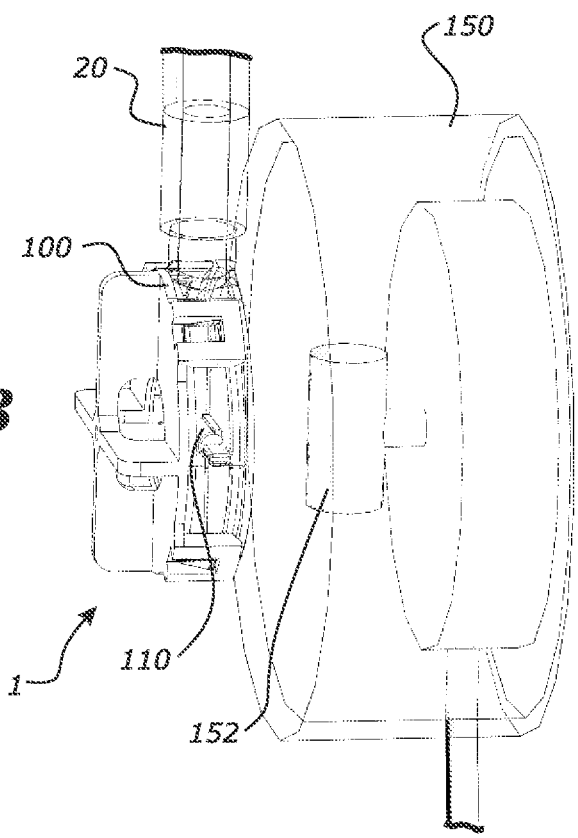
FIG. 5b shows a partial perspective view of a nutrient recycling device with a pump actuator with a magnetic driving element.

In one configuration, the movable member 108 at least partially comprises a magnetic or ferromagnetic element 110 as shown in FIGS. 3B, 3C, and 5B. In one configuration, the moveable member 108 is at least partially magnetic or ferromagnetic.

Alternatively, the moveable member 108 comprises a separable magnetic or ferromagnetic element 110. The magnetic or ferromagnetic element 110 is configured to be coupled with a complimentary magnetic or ferromagnetic piece 152. The magnetic or ferromagnetic element 110 preferably moves as the complimentary magnetic or ferromagnetic piece 152 moves. In one configuration, the complimentary magnetic or ferromagnetic piece 152 rotates. Preferably, the magnetic or ferromagnetic element 110 of the pump also rotates as the complimentary magnetic piece 152 rotates.

Preferably, the pump 100 is adapted to be driven by an external pump actuator 150. A pump actuator 150 external to the sealed bag 10 (described in more detail later), reduces the likelihood of the leakages.

In the preferred configuration, the magnetic element 110 comprises a cylindrical shape as best shown in FIG. 3B. It is anticipated, the magnetic or ferromagnetic element 110 may comprise other shapes such as a spherical or rectangular shape.

Preferably, the pump 100 comprises a durable biocompatible medical grade plastic. Preferably, the pump 100 is tolerant to a fluid environment, digestive enzymes and pH between 5.5-8.

Optionally, the pump 100 comprises a biofilm-resistant covering, or an antibacterial surface. An antibacterial covering or surface may be advantageous as in some configurations the pump 100 is submerged in digestive content 6.

Preferably, the pump 100 comprises material configured to be easily sterilised e.g. by gamma sterilisation.

In the preferred configuration, the pump 100 comprises a support 111 along the axis of rotation. Preferably the support 111 extends from the underside of the movable component 108.

As shown in FIG. 3C the bottom housing 106 optionally comprises a complimentary orifice 112 adapted to receive the support 111. Preferably, the support 111 and complimentary orifice 112 stabilises the movable component 108 as it moves.

Pump Locations

In one configuration, as shown in FIG. 4A, the pump 100 is located towards a lower end of the stoma bag 10.

Figure 4B:
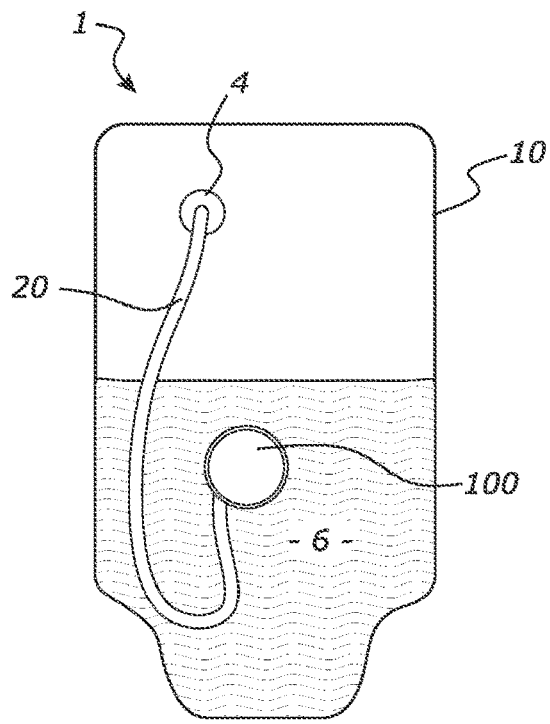
FIG. 4b shows a schematic of the nutrient recycling device with a pump located between the top and bottom of the bag.

In another configuration, as shown in FIG. 4B, the pump 100 is located between the top and bottom ends of the stoma bag 10.

In one configuration, the pump 100 is incorporated with the stoma bag 10 as it is located within the bag. An internal pump 100 is in fluid communication with the digestive contents 6. The material properties of the first conduit 20 and/or the pump 100 can bias the pump 100 towards the bottom of the stoma bag 10 (FIG. 4A). Material properties may include the flexibility of the first conduit 20, or the weight of the internal components.

Alternatively, the material properties of the first conduit 20 and/or the pump 100 can allow the pump 100 to float or partially float in the digestive contents 6 in the stoma bag 10 (FIG. 4B). For the avoidance of doubt, the use of the word float means not attached to the bag in this context. It is intended that the pump 100 will be fully or partially immersed in the digestive contents 6, as the bag 10 fills.

Figure 4C:
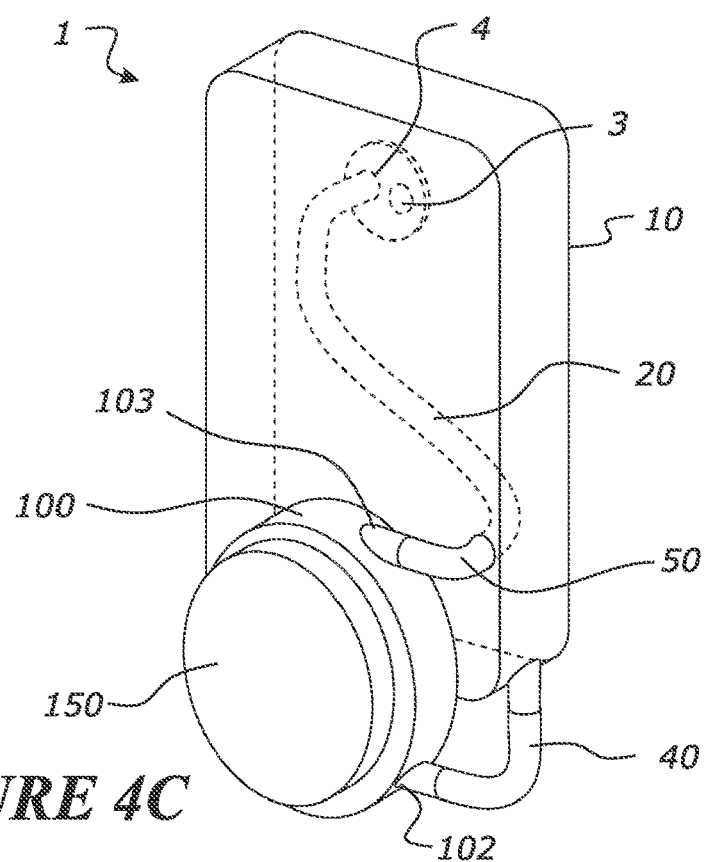
FIG. 4c shows a perspective view of a nutrient recycling device with a pump located external to the bag.

In another configuration, the pump 100 is located external to the stoma bag 10 as shown in FIG. 4C.

Preferably, the external pump 100 comprises a pump inlet 102 which receives the digestive contents 6 from the stoma bag 10.

Optionally, a first external conduit 40 connects the stoma bag 10 to the external pump 100. Preferably, the first external conduit 40 is connected at or towards the bottom of the stoma bag 10. Optionally, gravity helps deliver the digestive contents 6 from the stoma bag 10 to the external pump 100 if the first external conduit 40 is connected at or towards the bottom of the stoma bag 10.

Preferably, the stoma bag 10 comprises a first conduit opening adapted to allow the first external conduit 40 to communicate with the inside and the outside of the bag. Preferably, the first conduit opening is sealed against the first external conduit to prevent leakage from within the bag.

Preferably, the external pump 100 comprises a pump outlet 103 adapted to release the digestive contents 6 from the stoma bag 10. Optionally, a second external conduit 50 connects the pump outlet 103 to the stoma bag 10. Preferably, the stoma bag 10 comprises a second conduit opening adapted to allow the second external conduit 40 to communicate with the inside and the outside of the bag 10. Preferably, the second conduit opening is sealed against the second external conduit 40 to prevent leakage from within the bag 10.

Optionally, the external pump 100 is separable from the stoma bag 10. Preferably, inlet and/or outlets of the stoma bag 10 configured to lead to and from the external pump 100 comprises a one way valve or closing mechanism to prevent communication of digestive contents 6 when the external pump 100 is not connected.

Preferably, the stoma bag 10 comprises a second bag opening configured to allow communication of digestive contents to an external pump 100.

Optionally, the stoma bag 10 comprises a sealing plate. The sealing plate preferably comprises an aperture configured to be located at the second bag opening. The sealing plate is configured to allow passage of wires or other internal bag components to an external pump 100. The sealing plate preferably allows passage of these components while precluding leakage of the digestive contents 6 from within the stoma bag 10.

Incorporated Pump

The pump 100 can be incorporated into the stoma bag 10 by being attached to a side wall of the bag 10. In one configuration, the pump 100 is attached to the inner side wall of the bag 10. In another configuration, the pump 100 is attached to the outer side wall of the bag 10.

In another configuration, the pump housing forms at least part of the bag wall.

In one configuration, the pump 100 can be adhered to the side wall of the stoma bag 10 by plastic welding, chemical adhesion or other similar adhesion methods known in the art.

In another configuration, the pump 100 is incorporated into the stoma bag 10 by fastening means such as clips, clasps, buckles, Velcro, zip, slide fastener, snap fasteners, magnets or other fasteners known in the art.

Optionally, the pump 100 comprises a slit in its housing which engages with a complementary flange on the stoma bag 10 to secure the pump 100 to the bag 10.

In yet another configuration, the stoma bag 10 comprises a pouch (not shown) adapted to locate the pump 100 at the desired position relative to the stoma bag. Preferably, the pouch incorporated into a side wall of the stoma bag 10. In the preferred configuration, the pouch comprises a pouch opening to allow fluid communication between the digestive contents 6 and the pump 100. In another configuration, the inner side wall of the stoma bag 10 comprises a collar or clasp configured to clasp around the conduit 20. It is anticipated that other clasp, wrapping or fastening mechanism from within the stoma bag 10 can be used to position the pump 100 within the stoma bag 10.

Preferably, the side compartment adapted to store the pump 100 is located at or towards the pump 100, so the pump actuator 150 and the pump 100 can be in close contact.

In another configuration, the stoma bag 10 comprises magnets adapted to attract the pump 100 in the desired location.

Puma Actuators

In the preferred configurations, the nutrient recycling device 1 comprises a pump actuator 150 as shown FIG. 4C and FIGS. 5A-5C to drive the pump 100. Preferably, a coupling mechanism couples the pump actuator 150 to the pump 100.

In the preferred configuration, a magnetic coupling couples the pump actuator 150 to the pump 100. Alternatively, a mechanical coupling couples the pump actuator 150 to the pump 100.

In the preferred configuration, as represented in FIGS. 5A-5B, the pump actuator 150 is separable from the pump 100. A separable pump actuator 150 can be advantageous to keep the nutrient recycling device 1 compact, and lightweight which may be important to a patient as they may need to wear the nutrient recycling device 1 for extended periods of time.

In the preferred configurations, when in use, the pump actuator 150 engages with the pump 100 or is placed in close proximity to the pump by the patient. In one configuration, the patient connects the pump actuator 150 to the pump. In another configuration, the patient places the pump actuator 150 in close proximity to the pump in order for coupling between the pump actuator 150 and pump to drive the pump.

Alternatively, as represented in FIG. 4C, the pump actuator 150 can be integrated with the pump 100. This may be advantageous, as the nutrient recycling device 1 is a one unit device so to limit the management required by the patient or medical caretakers.

Optionally, the component comprising the pump actuator 150 comprises an integrated battery. The patient can replace the batteries when they run flat, or optionally they can charge the pump actuator unit separately.

Optionally, as shown in FIG. 5A, the pump actuator 150 comprises a power cord 151. Preferably the power cord 151 temporarily connects the nutrient recycling device 1 to an electricity supply. Optionally, the power cord 151 is a mains cable, adapted to be connected to a wall socket. Alternatively, the power cord 151 can be adapted to be connected to a USB or similar port, and may be powered by a portable power bank or other battery-like supply. Optionally, the power cord 151 is connected to a portable power supply such as a battery pack. The portable power supply can optionally be carried by the patient close to the stoma bag on their belt for example. The power supply can be worn on their belt by a clip or other fastening means, or in a separate pouch, or in a pouch incorporated on an outer side wall of the stoma bag 10. A portable power supply mechanism may be advantageous, to allow a patient to power their nutrient recycling device 1 conveniently.

Magnetic Pump Actuator

In one configuration as shown in FIG. 5A & 5B, the pump actuator 150 is a magnetically driven pump actuator. Preferably, an impeller is driven by a magnetic coupling between the magnetic pump actuator and the impeller.

Preferably, the pump actuator 150 comprises a complimentary driving magnet 152 which drives the magnetic piece 110 of the pump 100. Preferably, the magnetic piece 110 of the pump 100 is attracted to the driving magnet 152 of the pump actuator 150. As the driving magnet 152 of the pump actuator 150 rotates, so does the magnetic piece 110 of the pump 100. Preferably as the magnetic piece 110 rotates, the impeller 108 of the pump 100 also rotates to move the digestive contents 6 in the stoma bag 10.

An advantage of a magnetic coupling between the pump 100 and pump actuator 150, is that there can be no penetration through the bag 10. This pump 100 and pump actuator 150 arrangement may help improve the reliability of the nutrient recycling device 1 and may reduce complexity (especially of disposable parts). The nutrient recycling device 1 may also be attractive to the patient as they will not need to handle the digestive contents 6 to drive the pump 100.

This is an important aspect making the device convenient and easy to use. As the patient brings the pump actuator component 150 close to the pump component 100, they will be attracted to each other which makes coupling the two components quick and easy. Detaching the pump actuator 150 is also simple with a magnetic arrangement.

In the preferred configuration, the pump 100 with a magnetic element 110 and a separate corresponding pump actuator 150 provides a clear separation of internal stoma bag components and external components. This configuration may help ensure that the nutrient recycling device 1 is leak-proof. Furthermore, a nutrient recycling device 1 comprising separable internal and external parts may be advantageous, as disposable parts such as the stoma bag 10 can be easily replaced.

In some configurations, the power of the pump actuator 150 can be controlled. Preferably, the device 1 comprises a controller to increase or decrease the flow rate of the digestive contents 6. For example, a lower flow rate may be desired for neonates.

Optionally, the nutrient recycling device 1 comprises a flow meter configured to measure the function of the pump 100 and the flow of the digestive contents 6. This may be useful to determine whether the pump needs maintenance.

The nutrient recycling device 1 comprises a timer adapted to show how much time has elapsed since the pump was last use. This may be useful to help determine when the pump 100 should be turned on, especially if the nutrient recycling device 1 is operated manually. This may help prevent excessive bacterial contents accumulating in the bag 10.

Mechanical Pump Actuator

Figure 5C:
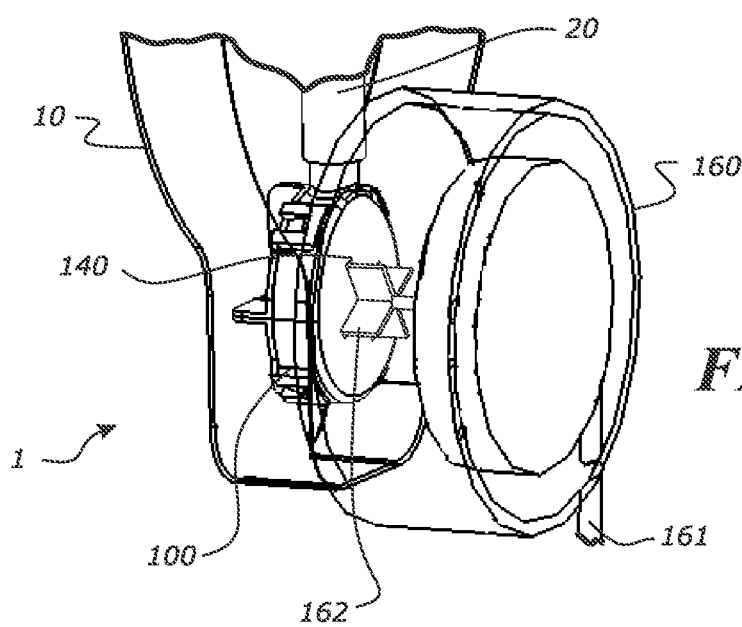
FIG. 5c shows a partial perspective view of a nutrient recycling device with a pump actuator with a mechanical driving element.

In another configuration as shown in FIG. 5C, the pump actuator 160 is mechanically coupled to the pump. Preferably, an impeller is driven by a mechanical coupling between the pump actuator 160 and the impeller.

Preferably, the pump 100 comprises an opening 140 adapted to receive a complimentary key piece 162 to drive the pump.

Preferably, the pump actuator 160 comprises the complimentary key piece 162.

The pump actuator key piece 162 mechanically engages with the pump opening 140. As the driving key piece 162 of the pump actuator 160 rotates, so does the pump 100. Preferably as the impeller 108 of the pump 100 rotates, the digestive contents 6 in the stoma bag 10 is driven towards the second conduit 20.

Manual/Automatic Operation

In one configuration, the patient or medical practitioner or caregiver can manually turn on the nutrient recycling device 1 on demand. Preferably the device runs continuously or runs from time to time to pump the digestive contents 6. Preferably, the digestive contents 6 are pumped towards the distal opening 4 of the ileum 2.

The nutrient recycling device 1 in some configurations comprises a switch, button, or can turn on the device by connecting it to a power supply. Optionally, the device 1 can be switched between an on-demand setting, or pre-set automatic settings.

In another configuration, the nutrient recycling device 1 can operate automatically. Preferably a controller operates to increase or decrease the flow rate of the digestive contests 6.

Preferably the controller can start and stop the operation of the pump 100. In one configuration the controller can be operated manually by a patient or a caregiver.

In another configuration the controller can operate automatically. This may be advantageous, if the patient wants the digestive contents 6 to be recycled at set intervals. For example, a night-time mode may be particularly advantageous, where the nutrient recycling device 1 operates automatically even when the patient is asleep.

A programmable controller may also be advantageous for customised delivery of the digestive contents 6 into a patient. For example, for patients with short bowel syndrome, or prior to ileostomy reversal surgery or other gastrointestinal disorders, individualised delivery of digestive contents 6 is preferably tailored to each patient to improve absorption of nutrients. The individualised delivery may be automated according to a programmable schedule tailored to each patient's needs.

Preferably, the pump 100 operates in a forward direction to pump the digestive contents 6 out of the bag. In some configurations, it may be desirable to reverse the pumping direction to clear blockages in the nutrient recycling device 1. Preferably, the pump operates in a reverse direction to clear blockages in the nutrient recycling device.

In one configuration, the pump 100 operates in a reverse direction from time to time to clear blockages in the nutrient recycling device.

In some configurations, the pump 100 operates in the reverse direction at the beginning of the cycle, and operates in a forward direction for the remainder of the cycle to pump the digestive contents 6 out of the bag 10.

In another configuration, the pump 100 operates in a reverse direction when a sensor detects a predetermined condition to clear blockages. This predetermined condition may indicate that the pump 100 is blocked, partially blocked, or when there is a reduced in flow of digestive contents 6.

In yet another configuration, the pump 100 alternates between a forward direction and a reverse direction to clear blockages in the nutrient recycling device.

In the preferred configurations, the pump 100 preferably provides substantively the same flow or pressure in each turn.

In the preferred configurations, the pump 100 provides substantially the same flow or pressure when operating in a forward direction and the reverse direction.

Optionally, different pump actuators can be used by the patient for different charging requirements. For example, a night-time pump actuator may be used to power the pump 100 at set intervals such as during the night-time. Another pump actuator 150 can be used by the patient to power the pump 100 on demand.

The nutrient recycling device 1 can be set to operate at set intervals. Preferably, the pump 100 operates every 10 minutes to 8 hours depending on what the patient requires. Preferably, the nutrient recycling device 1 is set to operate approximately every 30 minutes to 6 hours. Alternatively, the nutrient recycling device 1 operates continuously.

The nutrient recycling device 1 preferably operates for approximately 30 seconds to 20 minutes at a time or until the stoma bag 10 is emptied (fully or to a desired level).

Optionally, the nutrient recycling device 1 can be set to operate at a lower flow rate during times when the patient wants the device to be operating quietly, such as when they are sleeping or when they are in a public setting.

Optionally, the pump 100 is constantly connected to a power supply. This may be advantageous in cases where the pump function may need to be automated, or constantly running such as in the case of neonates in the intensive care unit. Optionally, the power supply can be attached to the side of an incubator or bed.

In some configurations, the pump 100 can operate at a low slow rate to reduce the chance of waking the patient through pump vibrations. A slow rate may also be beneficial for patients who experience sensations of fullness, discomfort or nausea with higher emptying rates.

Preferably, the digestive contents 6 is recycled often enough to prevent high growth rates of adverse bacteria within the stoma bag 10.

Optionally, the pump 100 is automatically activated after receiving certain outputs from a sensor. For example the pump 100 may be activated when a fluid level sensor, a bag weight sensor or an optical sensor detects when the bag 10 has reached a certain fullness. Alternatively the pump 100 may be activated when a sensor detects a certain amount of bacteria accumulated in the bag reaches a certain level.

Pump Actuator Attachment

The pump actuator 150 is incorporated with the stoma bag 10. In one configuration, the pump actuator 150 is located inside the bag. In another configuration, the pump actuator 150 is attached externally to the bag. Optionally, the pump 100 forms at least part of the bag wall.

In one configuration, the pump actuator 150 can be attached to a side wall of the bag (inside or outside). Preferably pump actuator 150 is attached to the outer side wall of the bag.

In one configuration, the pump 100 is located inside the bag 10 and the pump actuator 150 is located external to the bag 10. This may be advantageous as the pump actuator 150 is not in contact with the digestive contents 6 and remains clean, while being able to drive the pump 100 from outside the bag 10.

In another configuration, the stoma bag 10 comprises a pouch adapted to store the pump actuator 150. Preferably, the pouch is incorporated into a side wall of the stoma bag 10. It may be advantageous for a pump actuator 150 to be attached to the stoma bag 10, in particular such as for patients who operate the pump 100 in an automated mode, such as use overnight. Some patients with high outputs, fistulas, and arthritis, or poor vision may also benefit from a pump actuator 150 attached to the stoma bag 10.

In yet another configuration, the pump actuator 150 is incorporated with the stoma bag 10 by fastening means such as clips, clasps, buckles, Velcro, zip, slide fastener, snap fasteners, magnets or other fasteners known in the art.

Optionally, the pump actuator 150 can be adhered to the side wall of the stoma bag 10 by adhesion methods known in the art.

In another configuration, the stoma bag 10 comprises magnets adapted to attract the pump actuator 150 in the desired location.

Optionally, the pump actuator 150 is incorporated with the pump 100 as shown in FIG. 4C, and it can be powered by a separate power cord. In one configuration, the pump 100 and pump actuator 150 components are external to the stoma bag 10 as shown. Alternatively, the pump 100 and pump actuator 150 components are internal to the stoma bag 10. Optionally, a power cable is provided external to the stoma bag 10.

Preferably the pump actuator 150 is located in close proximity to the pump 100.

Peristaltic Pump

In another configuration, the nutrient recycling device 1 comprises a peristaltic pump 200 as shown in FIG. 6. The peristaltic pump 200 comprises a body 201, with a pump inlet 202. Preferably, the pump inlet 202 is located at or towards the bottom of the stoma bag 10.

Preferably, the peristaltic pump 200 is located within the stoma bag 10 so the pump is in fluid communication with the digestive contents 6.

Alternatively, the peristaltic pump 200 is located external to the stoma bag 10. Optionally, an external peristaltic pump 200 is connected to the stoma bag 10 by external conduits.

In the preferred configuration, the peristaltic pump 200 comprises a pump conduit 203 located within the pump body 201. Preferably, digestive contents 6 enter the pump conduit 203 through the pump inlet 202.

Preferably, the peristaltic pump 200 comprises an impeller 204 to drive the digestive contents 6 from a first end of pump conduit 203 to a second end. Preferably, the second end of the pump conduit 203 is connected or is continuous with a first conduit 220. Preferably the first conduit 220 connects the pump 200 to the distal opening 4 of the ileum 2.

Preferably, the impeller 204 comprises rollers 205. Preferably the rollers 205 are located towards the periphery of the pump. As the impeller 204 rotates, the rollers 205 compress the pump conduit 203 and pumps the digestive contents 6 in the direction of rotation to the outlet of the pump. The rollers 205 are configured to compress the pump conduit 203 to drive the digestive contents through the pump conduit.

Optionally, the impeller 204 is configured to grind up the digestive contents 6 into smaller particles, to reduce the chances of blockages.

Piston Pump

In another configuration, the nutrient recycling device 1 is a piston pump comprising a syringe pump 300 as shown in FIG. 7. The syringe pump 300 comprises a body 301, with a pump inlet 302. Preferably, the pump inlet 302 is located at or towards the bottom of the stoma bag 10.

Preferably, the syringe pump 300 is located or partially located external the stoma bag 10 so the patient or medical caregiver can operate a plunger 304 of the syringe.

Preferably, as the plunger 304 is pulled linearly along the inside of the body 301 to draw and eject digestive contents 6. Preferably, as the plunger 304 is pulled, digestive contents 6 is drawn into the plunger pump 300 through the inlet 302.

As the plunger 304 is pushed, digestive contents 6 is forced through an outlet 303. Preferably as the plunger 304 is pushed, the digestive contents 6 is forced through a first conduit 320. Preferably the first conduit 320 connects the syringe pump 300 to the distal opening 4 of the ileum 2. Preferably the syringe pump 300 is configured to push the digestive contents 6 to the distal opening 4 of the ileum 2.

In the preferred configuration, the plunger pump 300 comprises one or more one-way valves within a flow channel 313. Preferably, the one-way valves are adapted to ensure that when the plunger 304 is pulled, digestive contents 6 is drawn into the plunger pump. Preferably, the one-way valves are also adapted to ensure that when the plunger 304 is pushed, digestive contents 6 are ejected towards the outlet 303.

Valve Pump

Figure 8:
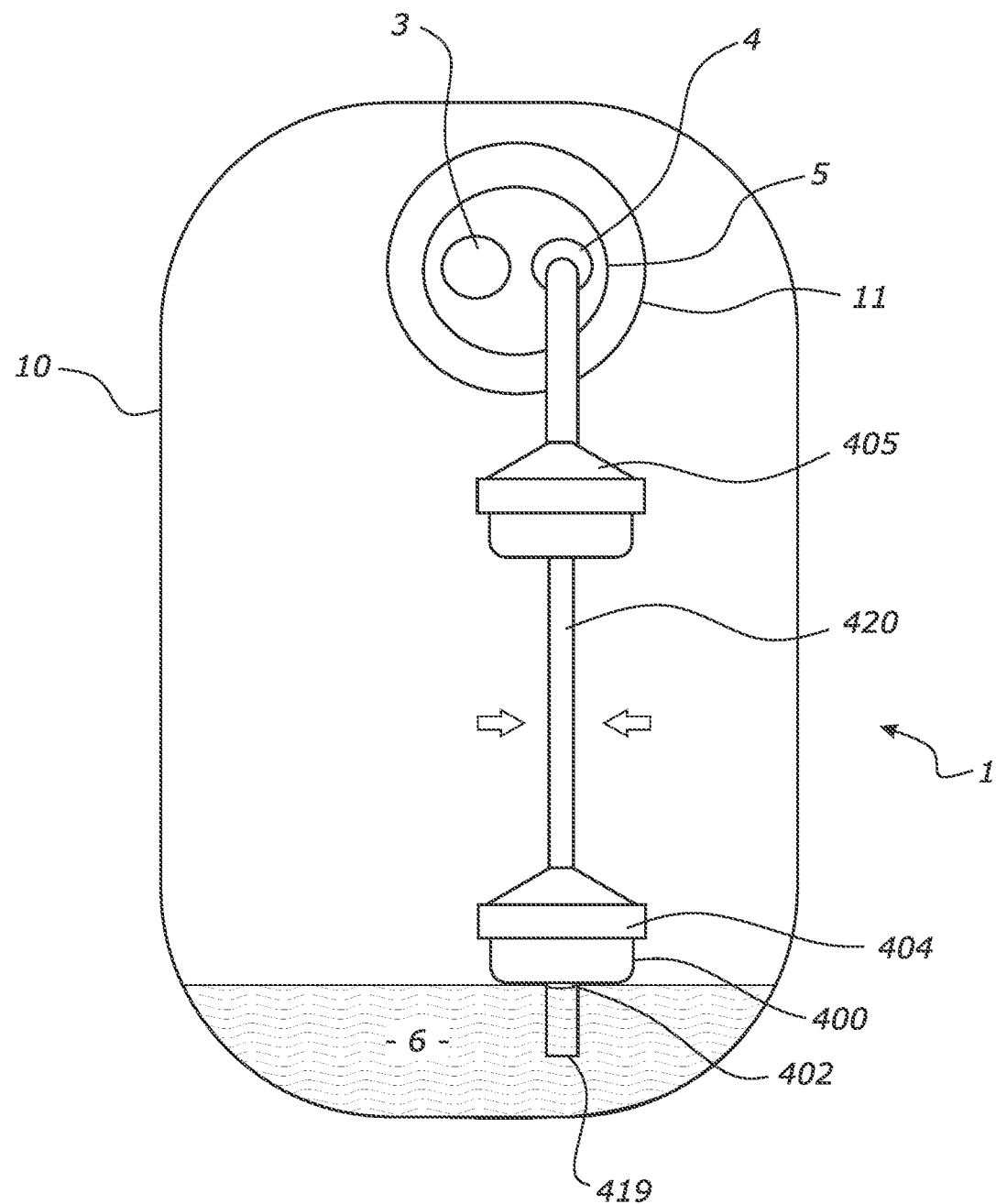
FIG. 8 shows a schematic of a nutrient recycling device with a valve pump.

In yet another configuration, the nutrient recycling device 1 comprises a valve pump 400 as shown in FIG. 8. The valve pump 400 comprises a pump inlet 402. Preferably, the pump inlet 402 is located at or towards the bottom of the stoma bag 10. Optionally, the valve pump 402 comprises an inlet conduit 419 to guide the digestive content 6 from within the stoma bag 10 to the inlet 402 of the pump.

Preferably, the valve pump 400 is located within the stoma bag 10 so the pump is in fluid communication with the digestive contents 6.

Preferably, the valve pump 400 comprises a first valve 404. Optionally, the valve pump 400 comprises a second valve 405.

Preferably, a first portion of the conduit 420 connects the valve pump 400 to the distal opening 4 of the ileum 2. The first portion of the conduit 420 is adapted to be compressed to drive the digestive contents towards the distal opening 4. Preferably, the first portion of the conduit 420 recoils after being compressed to suck further digestive contents 6 into the conduit for the next pump sequence.

A patient can manually do this by compressing the first conduit 420 through the stoma bag 10. The first valve 404 and/or second valve 405 prevents backflow of the digestive contents as the digestive contents are pumped up the first conduit 420.

Optionally, the nutrient recycling device 1 comprises a button or target configured to assist in compressing the first conduit 420.

Optionally, the nutrient recycling device comprises an external component adapted to assist in compressing the first portion of the conduit 420. Alternatively, an automated mechanism can be used to compress the conduit 420 at set intervals.

Optionally the nutrient recycling device 1 is constructed from a kit of parts.

Squeezable Bag

Figure 9A:
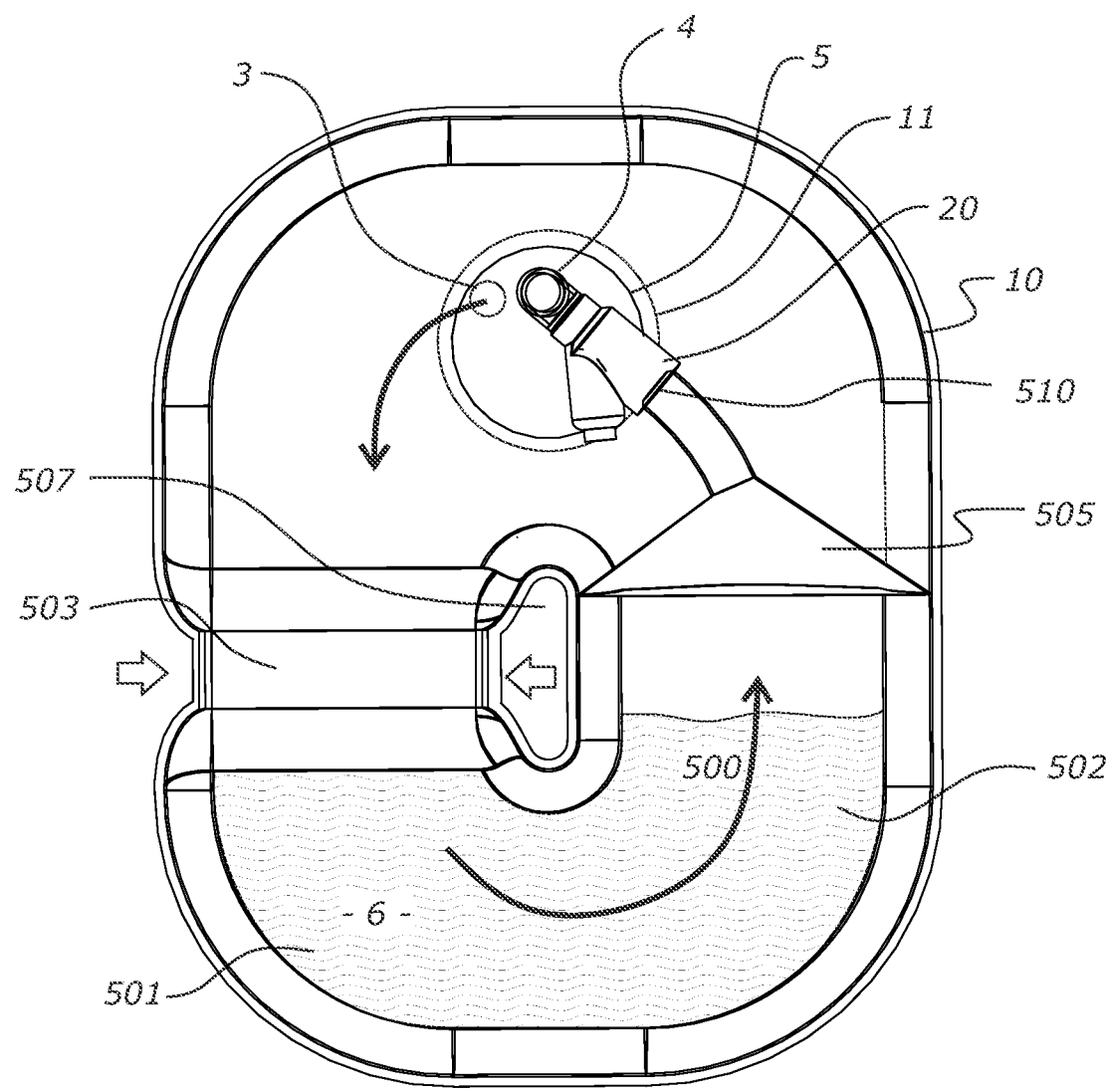
FIG. 9a shows a front view of a nutrient recycling device driven by compression.
Figure 9B:
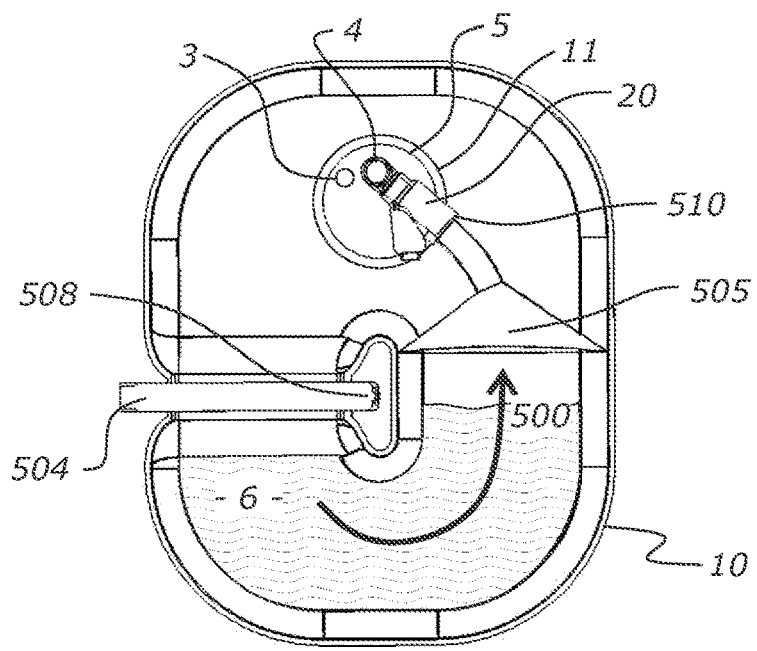
FIG. 9b shows a front view of a nutrient recycling device driven by compression including a clip.
Figure 9C:
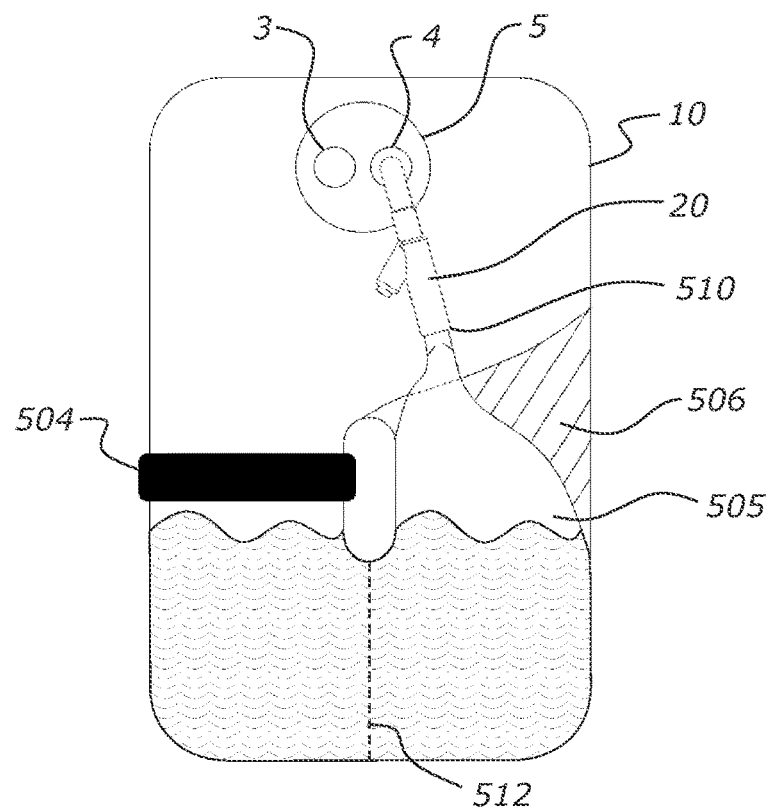
FIG. 9c shows a schematic of a nutrient recycling device driven by compression including a sealed section.

In some configurations, the nutrient recycling device 1 is configured to be pumped by manual manipulation of the bag 10 by the patient, caretaker, and/or medical practitioner as shown in FIGS. 9A-9C. In this configuration, at least a section of the bag 10 is configured to be externally compressed by a patient to pump the digestive contents 6 along a flow pathway 500. The flow pathway 500 preferably begins from or near the first bag opening 3, and leads to the distal opening 4 of the gastrointestinal tract.

In the preferred configurations, the pumping of waste is achieved by manual compression of the bag 10, by a patient, to drive the digestive contents 6 in a desired flow pathway as illustrated by arrow 500 in FIG. 9A. The pathway comprises a pathway inlet configured to receive digestive contents 6 from the proximal opening. The pathway also comprises a pathway outlet connected to an outlet conduit 20 at a junction 510. Preferably, the junction 510 between the pathway outlet and the outlet conduit 20 is located within the bag 10.

In this configuration, the bag 10 itself forms the pump body. In some configurations, the patient uses their hands to compress segments of the bag 10 to drive the digestive contents 6 towards the outlet conduit 20, leading to the distal opening 4 of the ileum 2. In other configurations, the patient may use a compression aid 504 to compress and drive the digestive contents 6 to the outlet conduit 20 (later discussed).

Preferably, the bag 10 is configured to be manually compressed by a patient to drive the digestive contents 6 along a sealed pathway to or towards the outlet conduit 20 of the nutrient recycling device 1.

A first end of the outlet conduit 20 is preferably configured to receive digestive contents 6 from the bag 10. A second end of the outlet conduit 20 is preferably connected to the distal opening 4 of the ileum 2 to guide the digestive contents 6 to the distal gastrointestinal tract.

Preferably, the patient squeezes the bag 10 in a sliding motion to drive the digestive contents 6 to or towards the outlet conduit 20 of the nutrient recycling device 1.

In the preferred configuration, the stoma bag 10 is configured for pumping by manual compression comprises a flow pathway 500 in fluid communication with the first end of the outlet conduit 20. Preferably the nutrient recycling device 1 comprises a junction 510 where the flow pathway 500 leads to the outlet conduit 20.

Alternatively, the patient can compress the bag 10 repetitively. Preferably, each successive compression is located closer towards the outlet conduit 20, to drive the digestive contents 6 towards the outlet conduit 20.

As the patient compresses a segment of the bag 10, the sidewalls of the bag 10 move inwards, and towards each other to form a compression site 503 as shown in FIG. 9A. As the bag 10 is compressed, the volume of the bag reduces at the compression site 503, and an area of high pressure is formed. The digestive contents 6 are driven from the area of high pressure created by the compression of the bag 10 to an area of lower pressure. The area of lower pressure is preferably located downstream of the compression 503 closer towards the outlet conduit 20.

In another configuration, the patient can roll up the bottom of the bag 10 to direct digestive contents 6 towards the opening of the outlet conduit 20. As the bottom of the bag 10 is compressed an area of high pressure is created. The digestive contents are 6 driven to move upwards, to a lower pressure area. Optionally, a paddle or rod is attached to the bottom of the bag 10 to assist with rolling of the bag 10 and/or driving the digestive content 6 upwards.

To prevent backflow, the outlet conduit 20 leading to the distal opening 4 preferably comprises one or more one way valves to prevent backflow of the digestive contents 6.

The manual compression of the bag 10 by a patient can be a stand-alone pump to drive the digestive contents 6, or used in conjunction with the other pump mechanisms previously described, or other known pumps.

Optionally, in another configuration, the patient can manually manipulate the bag 10 by inverting the bag 10 to allow gravity to drive the digestive contents 6 to or towards the outlet conduit 20, leading to the distal opening 4 of the ileum 2.

Bag Shape

In the preferred configuration, the stoma bag 10 comprises a doughnut-shape. In this configuration, the bag 10 comprises an aperture 507 through the bag 10. Preferably, the bag 10 comprises a defined sealed pathway around the perimeter of the aperture 507.

An advantage of this shape is to partially separate regions of the bag 10 and to define a pathway 500 for the digestive contents 6. Preferably, the doughnut-shaped bag 10 separates a first region 501 and a second region 502.

The first region 501 of the bag 10 receives the digestive contents 6 from the proximal opening 3 of the ileum 2. Preferably, the patient drives the digestive contents 6 to a second region 502 of the bag 10. The second region 502 of the bag 10 provides a pathway 500 to or towards the outlet conduit 20.

In the preferred configuration, the aperture 507 provides a convenient place to attach a clip 504 to prevent backflow (discussed later).

In some configurations, the aperture 507 of the bag 10 may be used to allow the patient to easily put their fingers through and grip around a segment of the bag 10 and to compress the bag 10 to drive the digestive contents 6 in the preferred flow pathway 500.

In the preferred configurations, the aperture 5 is positioned near the centre horizontally, to separate the first region 501 and a second region 502 substantially evenly.

In the preferred configurations, the aperture 5 is positioned below the stoma 5 (and the first and second opening of the gastrointestinal tract) so that the digestive contents 6 can enter the inside of the bag 10 and be guided into the desired pathway. Preferably, the aperture 507 is positioned near the stoma opening 5 to allow a large area for collecting digestive contents 6 while providing for separate regions in the bag 10.

In other configurations, where there is not an aperture 507 to separate the first region 501 and the second region 502, opposite internal sidewalls of the bag 10 can be joined together to separate the first region 501 and second region 502 of the bag 10. For example, opposite internal sidewalls of the bag 10 can be plastic welded together to separate regions of the bag 10. Preferably, opposite internal side walls along a longitudinal axis of the bag are joined together to separate the separate regions of the bag 10.

The doughnut-shaped bag 10 is preferably positioned over a stoma 5 of a patient. Preferably, a top section of the bag 10 is positioned over the stoma 5. The doughnut-shaped bag 10 covering a stoma 5 may be advantageous, as the bag 10 allows access to the proximal opening 3 and distal opening 4 of the gastrointestinal tract when it is in use, while closing the internal contents 6 of the bag off from the rest of its surroundings.

In yet another configuration, the bag 10 forms a U-shape, as a first end of the bag 10 is connected to the proximal opening 3 of the ileum 2, and a second end of the bag 10 is connected to the distal opening 4 of the ileum 2. A U-shape bag 10, like a doughnut-shaped bag 10 allows the patient to easily grip around segments of the bag 10 to drive the digestive contents 6 in the preferred flow pathway 500.

In some configurations, the bag 10 is a flexible tube which connects the proximal opening 3 of the ileum 2, to the distal opening 4 of the ileum 2. The flexible tube is adapted to be compressed by the patient to drive the digestive contents 6 to or towards the outlet conduit 20. A nutrient recycling device 1 comprising a flexible tube, external to a patient's body, connecting to the proximal opening 3 and the distal opening 4 of the ileum imitates the small intestine 2.

In another configuration, the bag 10 comprises a lower section comprising a smaller width than the upper section of the bag 10. A bag 10 comprising a tapered lower region may be beneficial where the patient compresses the bottom of the bag 10 to pump the digestive contents 6 upwards. A tapered lower region can make squeezing easier for patients, or more efficient as the digestive contents 6 are driven from an area of high pressure in the compressed lower region, to an area of low pressure in an upper region of the bag 10.

The tapered lower region can be a bulb or bladder shape.

Optionally, the tapered lower region of the bag 10 comprises, or is covered by a secondary material such as rubber to make squeezing more efficient. Optionally, the tapered lower region of the bag 10 comprises a textured surface to make squeezing more efficient.

In other configurations, the patient compresses a stoma bag 10 comprising a substantially rectangular, rounded rectangular, or oval shape.

Clip

In the preferred configurations, the nutrient recycling device 1 comprises a clip 504. In the preferred configuration, the clip 504 is externally attached to the bag 10 of the nutrient recycling device 1 as shown in FIG. 9B.

The clip 504 can be used by a patient to compress a segment of the bag 10, forming a compression site 503. The clip 504 preferably separates an upstream region and a downstream region of the bag 10, and limits flow from travelling upstream of the clip. Preferably the clip 504 limits digestive content 6 travelling back upstream towards the proximal opening 3.

The clip 504 is configured to isolate high pressure areas and desired low pressure areas from each other when the bag 10 is compressed. As the bag 10 is compressed, the clip 504 preferably allows the region downstream the clip to be pressurised, while isolating the upstream region. Preferably, the region upstream of the clip 504 maintains a lower pressure than the downstream region. It is advantageous to isolate the upstream and downstream regions of the clip 504, to limit the risk of detaching the nutrient recycling device 1 from a patient, during compression of the bag 10, due to potential high pressure at the stoma 5 attachment site.

Preferably the compression site 503 is formed close to, or at the level the digestive contents 6 rests when it is collected at the bottom of the bag 10.

In the preferred configuration, the clip 504, forms a first end of the pathway 500. Preferably, the patient manually compresses a segment of the bag 10 downstream the clip 504, towards the outlet conduit 20.

The clip 504 may also be beneficial to assist in directing the digestive contents 6 along the desired flow pathway 500, towards the opening of the outlet conduit 20.

The clip 504 preferably prevents back flow of the digestive contents 6, when a segment of the bag 10 is manually compressed. When the bag 10 is compressed, the clip 504 preferably prevents or reduces the volume of digestive contents 6 flowing upstream, towards the proximal opening 3. Instead, the digestive contents 6 are limited to flow in the desired flow pathway 500, towards the opening of the outlet conduit 20. Preferably, as the bag 10 is compressed, the digestive contents 6 are driven from the area of high pressure created by the compression of the bag 10, away from the clip 504, to an area of lower pressure. The area of lower pressure is preferably located closer towards the outlet conduit 20.

Preferably, the clip 504 is removably attached to the bag 10. The clip 504 can be removed once the patient has finished emptying the digestive contents 6 by driving the digestive contents to the outlet conduit 20. This may be advantageous, as the patient may be able to wear the bag 10 on its own without any attachments.

In the preferred embodiment as shown in FIG. 9B, the clip 504 comprises two adjacent clip legs. Preferably, the clip legs are movable relative to one another. Each clip leg is configured to be positioned on opposite outer sidewalls of the bag 10. The clip legs are configured to be pressed together to compress a segment of the bag 10, forming a compression site 503.

Preferably, the clip 504 comprises a securing means 508 configured to secure the two clip legs together. Optional, a first leg of the clip 504 comprises a female portion, and a second leg of the clip 504 comprises a male portion configured to fit together and secure the clip legs together.

Other securing means known in the art such as a drawstring may be used as an alternative to the clip 504.

Alternatively, the clip 504 can be attached to the bag 10 permanently, or semi-permanently. For example, in some configurations, a band which permanently encircles a segment of the bag 10 is used to prevent backflow.

Slider

In some configurations, the clip 504 can be used as a compression aid. In other configurations, an additional clip (not shown) can be used as a compression aid.

A compression aid 504 is preferably used by a patient to compress a segment of the bag 10, and drive the digestive contents 6 to or towards the outlet conduit 20

The compression aid 504 is preferably slidable, to drive digestive contents 6 towards the outlet conduit 20. Preferably the compression aid 504 drives the digestive contents 6 from a first region 501 of the bag 10 towards the second region 502 of the bag 10.

The compression aid 504 may be advantageous as it is able to compress the bag 10 and provide generally continuous pressure at the compression site 503. Preferably the compression aid 504 applies pressure across an entire width of the pathway 500, urging the bag walls together.

The compression site 503 is preferably easily maintained with the compression aid 504, even when it slides along the bag 10 to drive the digestive contents 6 along the flow pathway 500. The compression site 503 preferably shifts from a first region 501 towards second region 502 of the bag 10, as the compression aid 504 moves from the first region towards the second region.

The compression aid 504 preferably creates an area of high pressure in the bag, driving the digestive contents 6 to an area of lower pressure.

Preferably, the compression aid 504 also prevents back flow of the digestive contents 6. Preferably, the compression aid 504 or prevents the digestive contents 6 from flowing upstream of the compression aid 504, back towards the proximal opening 3.

Preferably, the compression aid 504 is removably attached to the bag 10. The compression aid 504 can be removed once the patient has finished emptying the digestive contents 6 by driving the digestive contents 6 to the outlet conduit 20. This may be advantageous, as the patient may be able to wear the bag 10 on its own without any attachments.

Alternatively, the compression aid 504 can be attached to the bag 10 permanently, or semi-permanently. For example, in some configurations, the compression aid 504 is a band which permanently encircles a segment of the bag 10.

Funnel

In the preferred configurations, an internal component of the bag 10 provides a pathway 500 towards the outlet conduit 20.

In some configurations, the bag 10 comprises a funnel 505 located inside the bag 10. The internal funnel 505 preferably converges towards the outlet conduit 20 configured to direct the digestive contents 6 towards the outlet conduit 20. The funnel 505 preferably comprises a wide inlet located towards the bottom of the bag 10 configured to receive the digestive contents 6. In some configurations the inlet of the funnel 505 is the width of the second region 502 of the bag 10. The inlet is located upstream from the outlet of the funnel.

Preferably, the funnel 505 is located towards the bottom of the bag 10, so that the inlet of the funnel is in fluid communication with the digestive contents 6 even when the bag 10 is only partially filled. This may be useful to limit occurrences of air being pumped through to the outlet conduit 20.

The funnel 505 preferably comprises a narrow outlet located at or towards the outlet conduit 20, configured to direct the contents of the bag 10 to or towards the outlet conduit 20. Preferably, the outlet of the funnel 505 is located downstream of the inlet.

In the preferred configuration as best shown in FIG. 9B, the funnel 505 is connected to the outlet conduit 20 forming a connection point, at the junction 510. Preferably the connection point 510 connects the flow pathway 500 to the outlet conduit 20, leading to the distal opening 4 of the ileum 2.

In the preferred configurations, the funnel 505 comprises integrated tubing configured to be connected to the outlet conduit 20 leading to the distal gastrointestinal tract.

Preferably, the funnel 505 comprises integrated tubing along the narrow region of the funnel. Integrated tubing may be advantageous as it can provide for a better connection between the funnel 505 and the outlet conduit 20.

In some configurations, the funnel 505 is created at least partially by welding opposing side walls of the bag 10 to form the shape of a funnel, to direct the flow of the digestive contents 6 to or towards the outlet conduit 20.

In other configurations, the funnel 505 is a component formed separate to the side walls of the bag 10. In some configurations, the separate funnel 505 is connected to the internal sidewall of the bag 10. Preferably, the funnel 505 is plastically welded to the internal sidewall of the bag 10. In other configurations, the funnel 505 is connected to the sidewalls of the bag 100 by other adhesion means known in the art.

Filter

In the preferred configurations, the bag 10 comprises a filter 512 as shown in FIG. 9C configured to separate finer digestive contents 6 from larger particulate matter.

The filter 512 is preferably a mesh which separates finer digestive contents 6 from larger particulate matter.

Preferably the filter 512 limits digestive content with a diameter larger than the outlet conduit 20 from passing through it.

Preferably, the filter 512 can help separate the bag 10 into sub-compartments. The digestive contents 6 pass through a first sub-compartment, and only finer particles enter a second sub-compartment, downstream from the first sub-compartment.

The advantage of a filter 512 is to limit the likelihood of the outlet conduit 20 from being blocked, as this may require medical attention or replacement of the component.

Optionally, the larger particulate matter isolated from the digestive contents 6 can be emptied from an opening in the bag 10.

In one configuration, the isolated particulate matter can be emptied from a drainage bag opening 13, preferably located at the bottom of the bag 10. In this configuration, patient only has to empty the ruminant larger particulate matter remaining in the bag, while most of the digestive contents 6 are regularly recycled to the distal gastrointestinal tract.

Optionally, the bag 10 comprises an opening located close to the filter 512 to allow filtered digestive contents 6 to be removed from inside of the bag 10. Preferably, the opening is resealable.

Alternatively, the patient can simply replace the bag 10 as required.

In the one embodiment, the filter 512 is located between the compression site 503 and the funnel 505. Preferably, the filter 512 is located in the bottom region of the bag 10 where the digestive matter 6 is generally collected. As the digestive contents 6 are driven from a first region 501 of the bag to a second region 502, the filter 512 separates different sized particles of the digestive content 6.

In another embodiment, the filter 512 is located in the upper first region 501 of the bag 10, towards the proximal opening 3. As the digestive contents 6 enter the bag 10 from the proximal opening 3, finer digestive contents 6 fall to the bottom of the bag 10 due to gravity. Preferably, larger particulate matter remains upstream of the filter 512.

Optionally, the filter 512 is located in the funnel 505. Preferably the filter 512 limits larger partially digested particulate matter from entering the narrower section of the funnel, and creating blockages. This may be advantageous, as a single internal component can be attached to the bag 10 with the dual function of directing digestive content 6 to the outlet conduit 20, while limiting blockages.

This configuration is advantageous as it may enable a patient to eat a generally unrestricted diet while still utilising the nutrient recycling device 1. Being able to eat a generally unrestricted diet while recycling nutrients will probably be attractive to patients.

As shown in FIG. 9C, in some configurations, the bag 10 comprises a sealed section 506 configured to direct the flow of the digestive contents 6 to the first region 501 of the bag 10. Preferably, the sealed section 506 is located in the second region 502 of the bag 10. The sealed section 506 seals opposite walls of the bag 10 together to prevent digestive contents 6 from entering the second region 502 from the top end of the bag 10. In some embodiments, an anticlockwise pathway is formed.

In some configurations, the sealed section 506 can be used to create the funnel 505 section during manufacture.

Outlet Conduit Connection

The nutrient recycling device 1 preferably comprises an outlet conduit 20 passing outside the bag 10, through the bag opening 11. Preferably, to allow good patient workflow, the outlet conduit 20 is easily connectable and dis-connectable from a second conduit 30 located in the distal gastrointestinal tract. This may be beneficial, as some patients may want to change the bag 10 of the nutrient recycling device 1 regularly.

To facilitate the replacement of the bag 10, a portion of the outlet conduit 20 extending outside the bag 10 for easy connection with the second conduit 30 which leads to the distal gastrointestinal tract may be useful.

Optionally, the second conduit 30 remains in the distal intestinal tract while the rest of the nutrient recycling device 1 can be removed for replacement, or maintenance.

Benefits

A nutrient recycling device 1 driven by the manual compression of the bag 10 is advantageous as the bag design reduces the likelihood of contamination. A bag 10 configured for manual compression does not communicate with additional components, which reduces the likelihood of leakage.

The pumping action occurs external to a sealed bag 10. As there are no internal components in contact with the digestive contents 6, this eliminates the risk of blockages which may occur with mechanical moving components.

Additionally, a nutrient recycling device 1 with limited components is simple and cheap to manufacture, and expected to be reliable. A nutrient recycling device 1 driven by the manual compression of the bag 10 can be cheaply replaced, and may be beneficial for patients who may want to replace their nutrient recycling device regularly.

The nutrient recycling device 1 is also relatively light, reducing the likelihood of leaks or detachments from the stoma 5.

Furthermore, as the nutrient recycling device 1 driven by the manual compression does not require external energy from batteries, or a pump, there is less risk of device failure. Furthermore, it is generally easier to obtain regulatory approval without mechanical components and therefore relatively easy for medical markets to introduce this configuration of the nutrient recycling device 1.

Further Advantages

An advantage of the nutrient recycling device 1 is that it is a partially external component, and is low-impact in nature. The device 1, is preferably not significantly more burdensome than wearing a traditional stoma bag.

Patients may find the device 1 attractive as in the preferred configurations the device is portable, and may be self-operated and/or managed at home. This is beneficial as some hospital resources can be saved as the patient can manage their own device.

In particular, some patients with low pump actuator control such as with hand arthritis, neurological disorders, or poor vision may find it difficult to manage emptying a stoma bag 10. The nutrient recycling device 1 may help enable these patients' independence, in-between assisted bag changes by a caregiver.

The digestive content recycling capabilities of the device 1 may additionally be advantageous, as this will decrease the need of a patient to regularly empty their stoma bag 10.

Additionally, regular recycling may reduce the risk of stoma bag leaks, which sometimes occur when the bags become overfull.

The nutrient recycling device 1 comprising a stoma bag 10 with an incorporated pump 100 can be easy to operate, and compact and simple to manufacture.

To those skilled in the art to which the invention relates, many changes in construction and widely differing embodiments and applications of the invention will suggest themselves without departing from the scope of the invention as defined in the appended claims.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

The invention claimed is:

1. A nutrient recycling device comprising:
   a flexible bag including a first bag opening and adapted to receive digestive contents from a first surgically created gastrointestinal tract opening through the first bag opening;
   a pump located within the flexible bag, or incorporated with the flexible bag by attachment to the flexible bag, the pump adapted to pump digestive contents received by the flexible bag to a second gastrointestinal tract opening; and a pump actuator separable from the pump and adapted to be operably coupled to the pump;

wherein the pump comprises a pump inlet in fluid communication with an interior of the flexible bag; and a pump outlet connected to an outlet conduit; and wherein the outlet conduit comprises a first portion and a second portion;

the first portion of the outlet conduit is located within the bag; and the second portion of the outlet conduit is located externally to the bag and adapted to be insertable into a gastrointestinal tract.

2. A nutrient recycling device as claimed in claim 1, wherein the second portion of the outlet conduit is adapted to be insertable into a gastrointestinal tract through the second gastrointestinal tract opening.

3. A nutrient recycling device as claimed in claim 1, wherein the first bag opening is configured to be positioned
   a) over the surgically created first gastrointestinal tract opening;
   b) over the first and second gastrointestinal tract openings; or
   c) over the surgically created first gastrointestinal tract opening, wherein the flexible bag includes a second bag opening configured to be positioned over the second gastrointestinal tract opening.

4. A nutrient recycling device as claimed in claim 1, wherein the flexible bag comprises an attachment portion configured to attach the bag to a patient, and wherein the attachment portion is an adhesive backing.

5. A nutrient recycling device as claimed in claim 4, wherein the attachment portion is separable from the flexible bag.

6. A nutrient recycling device as claimed in claim 1, wherein the pump
   a) is attached to an inside wall of the flexible bag;
   b) is attached to an external wall of the flexible bag; or
   c) forms at least part of the wall of the flexible bag.

7. A nutrient recycling device as claimed in claim 1, wherein the flexible bag further comprises at least one external conduit opening adapted to allow at least one external conduit to communicate between an inside and an outside of the flexible bag.

8. A nutrient recycling device as claimed in claim 1, wherein
   (1) the pump is attached to the flexible bag by one or more of
      a) clips;
      b) clasps;
      c) buckles;
      d) Velcro;
      e) Zip fastener;
      f) slide fastener;
      g) snap fasteners; and/or
      h) magnets;
      or
   (2) the bag includes a pouch adapted to locate the pump and wherein the pouch is incorporated into a side wall of the flexible bag.

9. A nutrient recycling device as claimed in claim 1, wherein the outlet conduit includes an output end positionable in the gastrointestinal tract downstream from the first gastrointestinal tract opening and is configured to reintroduce digestive contents back into a patient.

10. A nutrient recycling device as claimed in claim 1, wherein the outlet conduit includes an output end positionable in the gastrointestinal tract upstream from the first gastrointestinal tract opening and is configured to reintroduce digestive contents back into a patient.

11. A nutrient recycling device comprising:
   a flexible bag including a first bag opening and adapted to receive digestive contents from a first surgically created gastrointestinal tract opening through the first bag opening;
   a pump located within the flexible bag and adapted to pump digestive contents received by the flexible bag to a second gastrointestinal tract opening; and
   a pump actuator separable from the pump and adapted to be operably coupled to the pump;
   wherein the pump comprises
      a pump body and an impeller drivable by the pump actuator by a drive coupling between said pump actuator and said impeller;
      a pump inlet in fluid communication with an interior of the flexible bag; and
      a pump outlet connected to the outlet conduit.

12. A nutrient recycling device as claimed in claim 11, wherein the pump body is located inside the flexible bag and the pump actuator is located externally to the flexible bag.

13. A nutrient recycling device as claimed in claim 11, wherein the first bag opening is configured to be positioned
   a) over the surgically created first gastrointestinal tract opening;
   b) over the first and second gastrointestinal tract openings; or
   c) over the surgically created first gastrointestinal tract opening;
   wherein the flexible bag includes a second bag opening configured to be positioned over the second gastrointestinal tract opening.

14. A nutrient recycling device as claimed in claim 11, wherein the flexible bag comprises an attachment portion configured to attach the bag to a patient, and wherein the attachment portion is an adhesive backing.

15. A nutrient recycling device as claimed in claim 14, wherein the attachment portion is separable from the flexible bag.

16. A nutrient recycling device as claimed in claim 11, wherein the pump
   a) is attached to an inside wall of the flexible bag, or
   b) forms at least part of the wall of the flexible bag.

17. A nutrient recycling device as claimed in claim 11, wherein
   (1) the pump is attached to the flexible bag by one or more of
      a) clips;
      b) clasps;
      c) buckles;
      d) Velcro;
      e) Zip fastener;
      f) slide fastener;
      g) snap fasteners; and/or
      h) magnets;
      or
   (2) the bag includes a pouch adapted to locate the pump and wherein the pouch is incorporated into a side wall of the flexible bag.

18. A nutrient recycling device as claimed in claim 11, wherein said drive coupling is a magnetic coupling between said pump actuator and said impeller.

19. A nutrient recycling device as claimed in claim 11, wherein said drive coupling is a mechanical coupling between said pump actuator and said impeller.

20. A nutrient recycling device as claimed in claim 11, wherein the pump comprises a controller therefor and
   a) the controller is configured to increase or decrease a flow rate of digestive contents through the device;
   b) the controller is adapted to be operated manually by a patient;
   c) the controller is adapted to operate the pump automatically;
   d) the controller is adapted to operate the pump at set intervals;
   e) the controller is adapted to operate when a predetermined fluid level, bag weight, and/or bacteria level as detected by a sensor is reached;
   f) the controller is adapted to operate the pump in a reverse direction to clear blockages;
   g) the controller is adapted to operate the pump in a reverse periodically to clear blockages;
   h) the controller is adapted to operate the pump in a reverse direction to interior clear blockages when a sensor detects a predetermined condition; and/or
   i) the controller is adapted to operate the pump to alternate between a forward direction and a reverse direction to clear blockages.

21. A nutrient recycling device as claimed in claim 11, wherein the pump is configured to actively grind or cut digestive contents into smaller particles.

22. A nutrient recycling device as claimed in claim 11, wherein the pump floats freely within the flexible bag supported by the outlet conduit.

23. A nutrient recycling device as claimed in claim 11, wherein the pump comprises at least one one-way valve.

24. A method comprising:
   receiving digestive contents from a first surgically created gastrointestinal tract opening and pumping the digestive contents to a second gastrointestinal tract opening using a device comprising
      a flexible bag adapted to receive digestive contents from the first surgically created gastrointestinal tract opening through a first bag opening of the flexible bag;
      a pump located within the flexible bag adapted to pump digestive contents received by the flexible bag to a second gastrointestinal tract opening; and
      an outlet conduit adapted to define a flow pathway for digestive content to flow from the pump to the second gastrointestinal tract opening; and
      a pump actuator separable from the pump and adapted to be operably coupled to the pump;
   wherein the pump comprises
      a pump body and an impeller drivable by the pump actuator by a drive coupling between said pump actuator and said impeller;
      a pump inlet in fluid communication with an interior of the flexible bag; and
      a pump outlet connected to the outlet conduit;
   wherein the method further includes
      positioning the first bag opening over the first gastrointestinal tract opening or over the first and second gastrointestinal tract openings; and
      operating the device periodically to pump the digestive contents towards the second gastrointestinal tract opening.

25. A method as claimed in claim 24, wherein said second gastrointestinal tract opening is located upstream of the first surgically created gastrointestinal tract opening.

26. A method as claimed in claim 24, wherein said second gastrointestinal tract opening is located downstream of the first surgically created gastrointestinal tract opening.

27. A method as claimed in claim 24, further comprising holding the pump actuator in close proximity to the pump or connecting the pump actuator to the pump and thereby coupling the pump actuator and pump and driving the pump.

28. A method as claimed in claim 24, further including flowing the digestive contents through a flow pathway between the flexible bag and the second surgically created gastrointestinal tract opening a plurality of times to increase absorption by a patient of nutrients in the digestive contents.

29. A nutrient recycling device comprising:
   a flexible bag including a first bag opening and adapted to receive digestive contents from a first surgically created gastrointestinal tract opening through the first bag opening;
   a pump located within the flexible bag, or incorporated with the flexible bag by attachment to the flexible bag, the pump adapted to pump digestive contents received by the flexible bag to a second gastrointestinal tract opening; and
   a pump actuator separable from the pump comprising a syringe plunger external to the flexible bag and adapted to be operably coupled to the pump to push digestive contents towards the second gastrointestinal tract opening;
   wherein the pump comprises
      a pump inlet in fluid communication with an interior of the flexible bag; and
      a pump outlet connected to the outlet conduit.

30. A nutrient recycling device as claimed in claim 29, wherein the pump comprises at least one one-way valve.

* * * * *